United States Patent
Weiss et al.

(10) Patent No.: US 11,103,663 B2
(45) Date of Patent: Aug. 31, 2021

(54) MULTIPURPOSE PNEUMATIC ORAL INTERFACE

(71) Applicant: PTW Design & Development, Inc., Berkeley, CA (US)

(72) Inventors: Philip Weiss, Berkeley, CA (US); Richard Weiss, Berkeley, CA (US)

(73) Assignee: PTW DESIGN & DEVELOPMENT, INC., Berkeley, CA (US)

(*) Notice: Subject to any disclaimer, the term of this patent is extended or adjusted under 35 U.S.C. 154(b) by 206 days.

(21) Appl. No.: 16/398,176

(22) Filed: Apr. 29, 2019

(65) Prior Publication Data

US 2019/0328988 A1 Oct. 31, 2019

Related U.S. Application Data

(60) Provisional application No. 62/664,854, filed on Apr. 30, 2018.

(51) Int. Cl.
*A61M 16/04* (2006.01)
*A61C 17/08* (2006.01)

(52) U.S. Cl.
CPC ...... *A61M 16/049* (2014.02); *A61M 16/0493* (2014.02); *A61C 17/08* (2019.05); *A61M 2205/0216* (2013.01)

(58) Field of Classification Search
CPC ............ A61M 16/049; A61M 16/0493; A61M 2205/0216; A61M 2205/13; A61M 2205/3592; A61M 2205/3561; A61M 25/02; A61M 2205/502; A61M 2209/088
See application file for complete search history.

(56) References Cited

U.S. PATENT DOCUMENTS

| | | | | |
|---|---|---|---|---|
| 5,803,731 | A * | 9/1998 | Nordstrom | A61C 17/08 433/96 |
| 9,968,341 | B2 * | 5/2018 | Ritter | A61B 1/24 |
| 2010/0204624 | A1 * | 8/2010 | Vuillerme | A61F 9/08 601/46 |
| 2011/0270166 | A1 * | 11/2011 | Martin | A61H 21/00 604/79 |
| 2015/0173856 | A1 * | 6/2015 | Lowe | A61C 7/00 433/24 |
| 2016/0270878 | A1 * | 9/2016 | Fulton, III | A61B 1/24 |

FOREIGN PATENT DOCUMENTS

GB 894164 A * 4/1962 ............ A61C 17/08

* cited by examiner

*Primary Examiner* — Timothy A Stanis
*Assistant Examiner* — Matthew R Moon
(74) *Attorney, Agent, or Firm* — Kwan & Olynick LLP

(57) ABSTRACT

Various embodiments of the present disclosure relate to systems and apparatus for oral interfaces. According to particular embodiments, an oral interface comprises a body comprising a flow channel extending through the body from a first opening to a second opening. A lip commissure hook extends from a first end of the body in a curved configuration, and an intraoral portion extends from the lip commissure hook to form a gap between the intraoral portion and the body. An outer mandibular contact extends from the body. The flow channel extends through the lip commissure hook and the intraoral portion to the first opening and to a second opening located at a second end of the body. The intraoral portion and the outer mandibular contact are configured to apply frictional forces against the user's mandible and cheek to stabilize the oral interface upon the user.

20 Claims, 18 Drawing Sheets

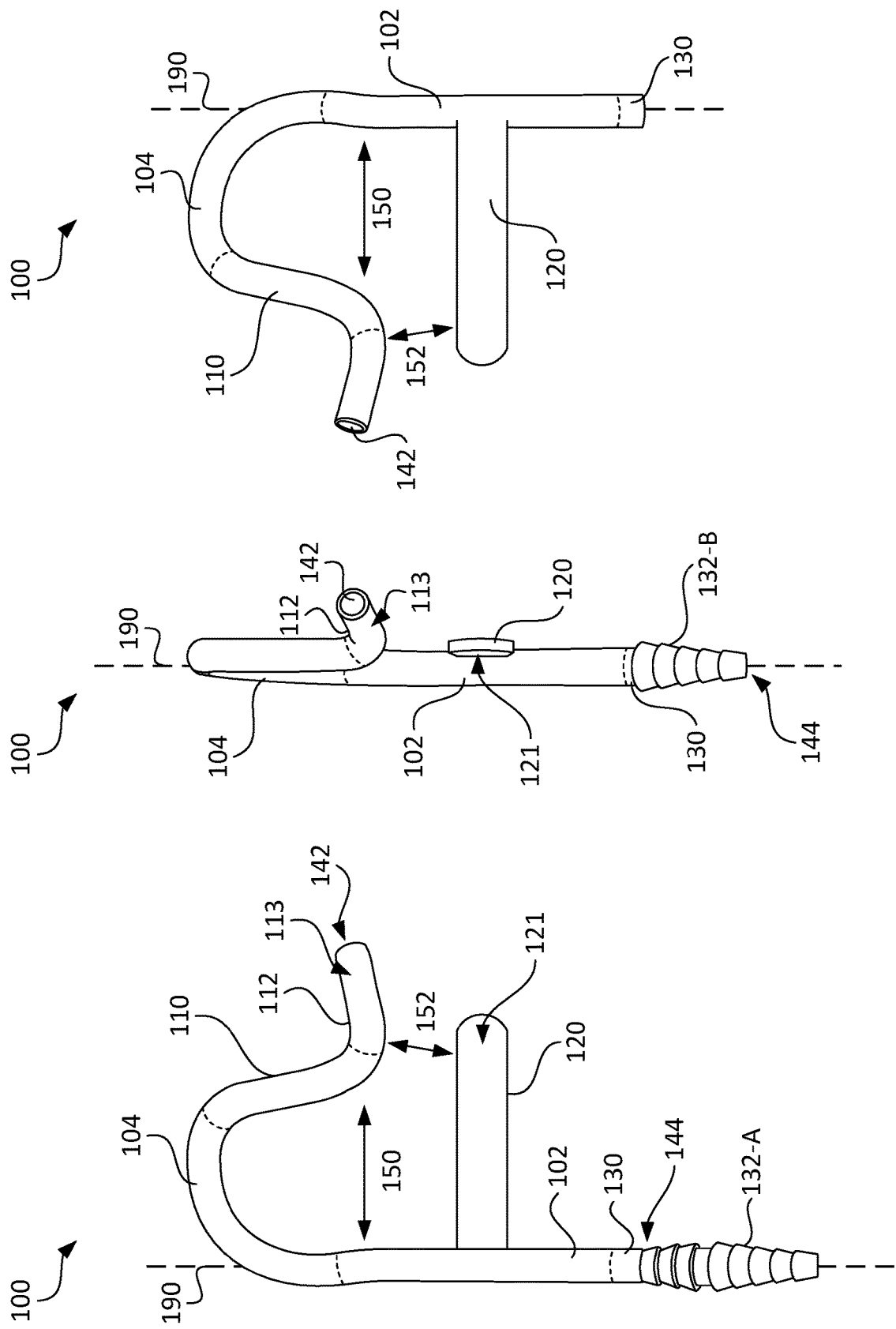

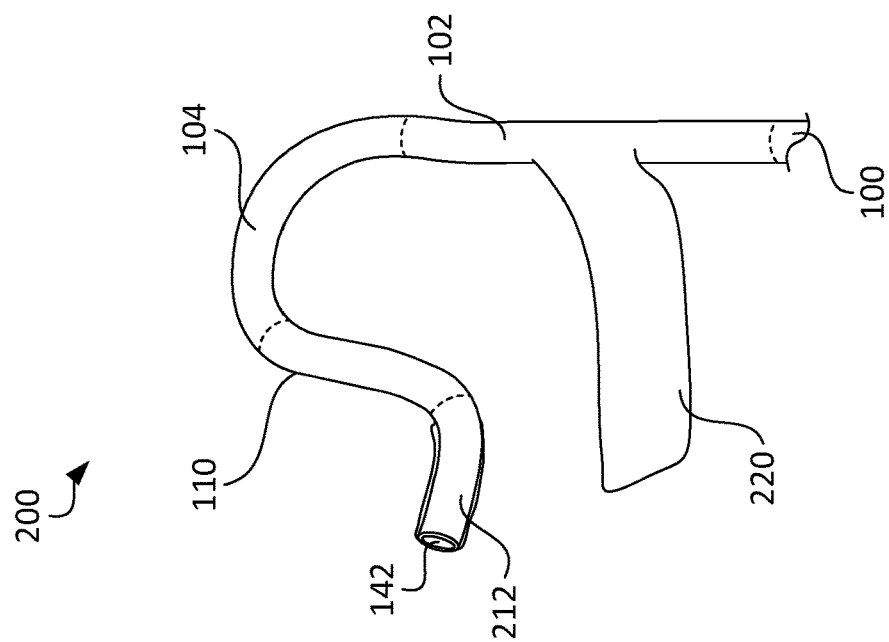
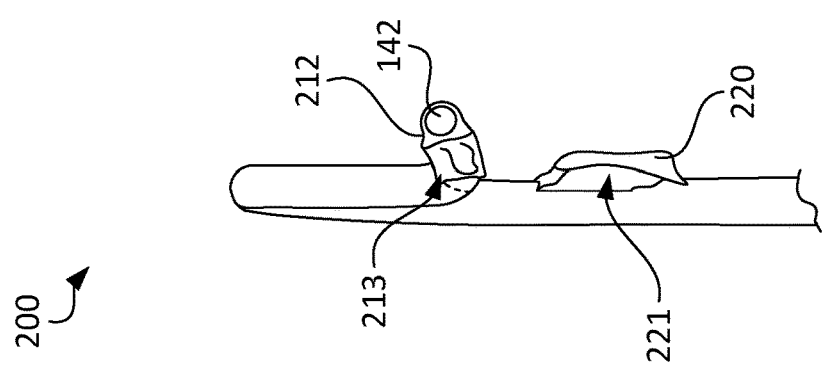
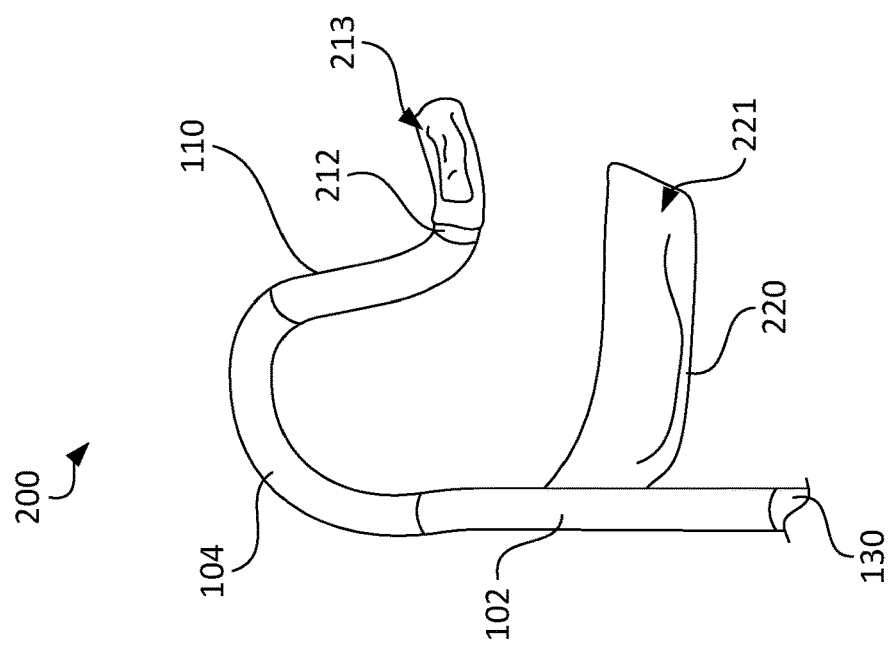

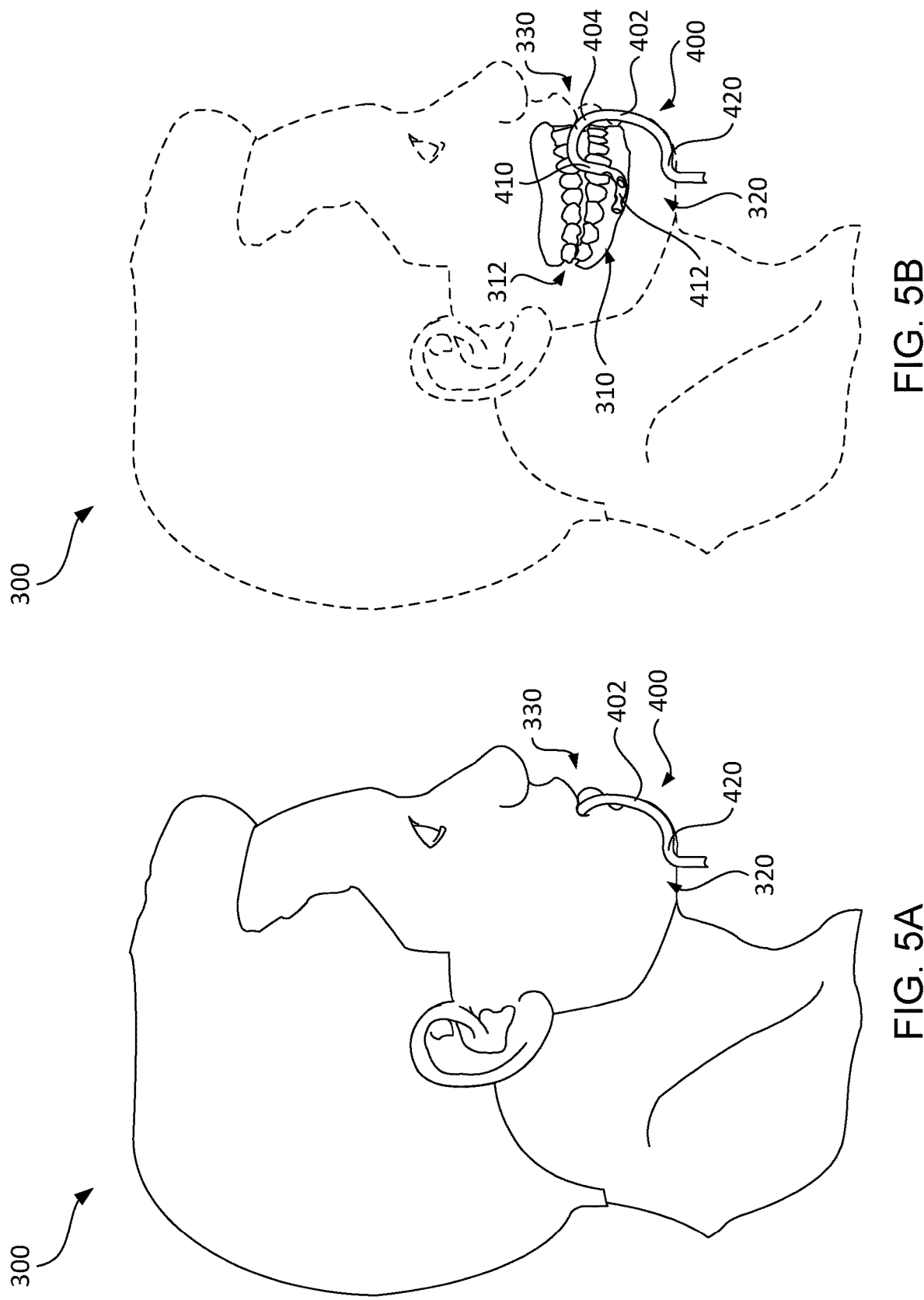

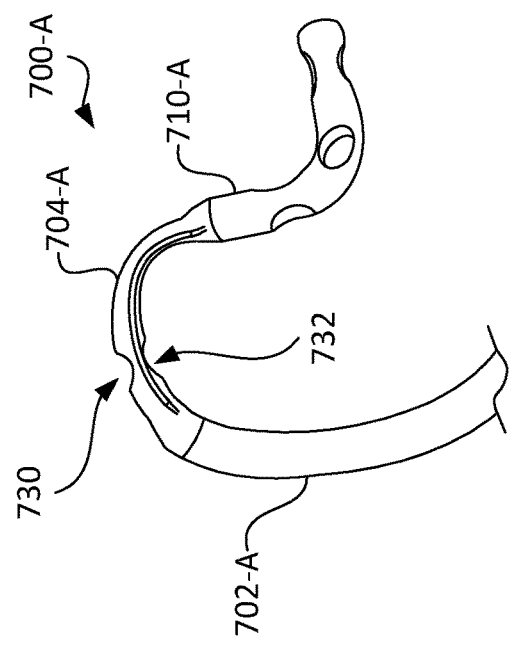
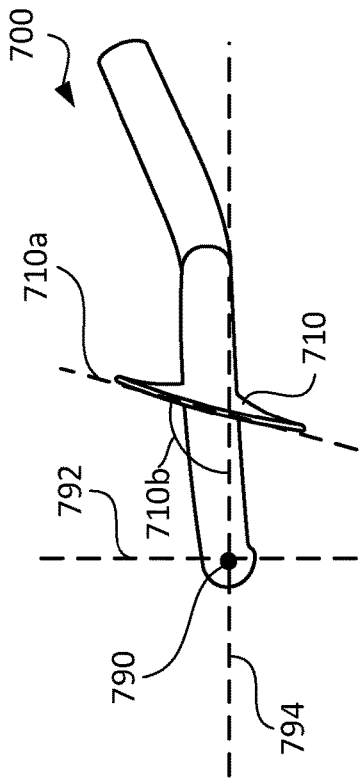
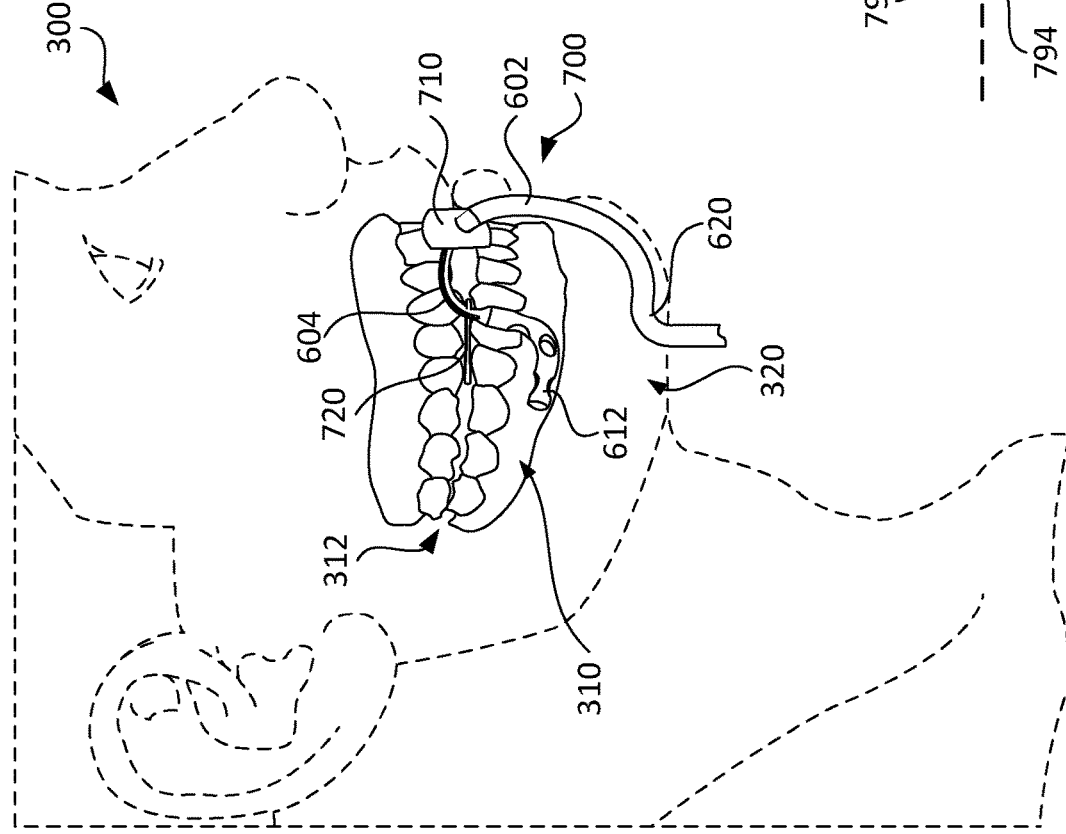
FIG. 7H
FIG. 7F
FIG. 7G

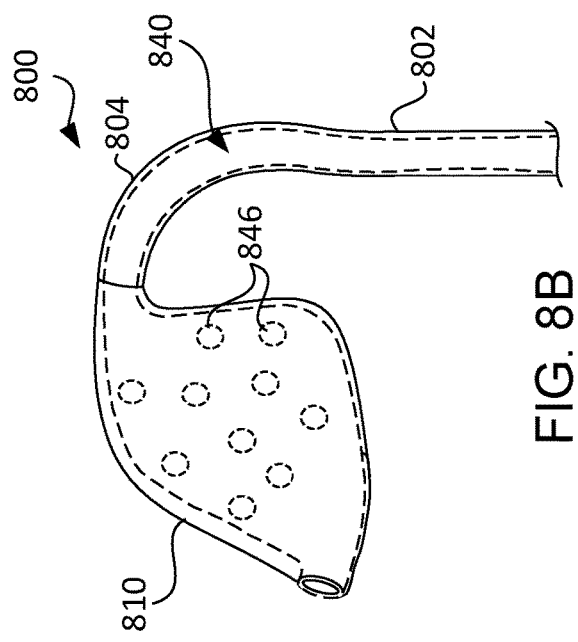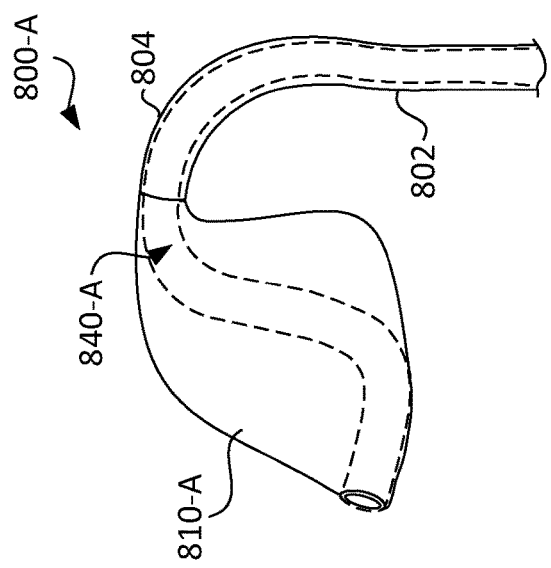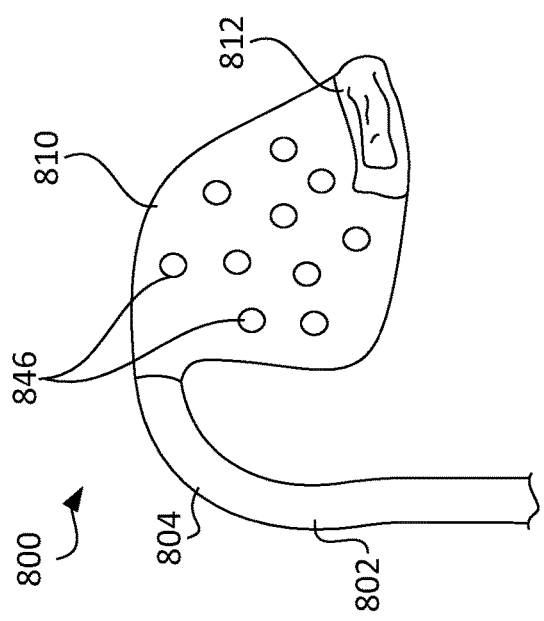

MULTIPURPOSE PNEUMATIC ORAL INTERFACE

CROSS-REFERENCE TO RELATED APPLICATIONS

This application claims priority under 35 U.S.C. § 119(e) to U.S. Provisional Application No. 62/664,854, filed Apr. 30, 2018, entitled MULTIPURPOSE PNEUMATIC ORAL INTERFACE, the contents of which are hereby incorporated by reference.

TECHNICAL FIELD

The present disclosure relates generally to oral interfaces, and more specifically to a multipurpose pneumatic oral interface for implementation with various breathing devices including ventilators and sip-and-puff (SNP) devices.

BACKGROUND

Non-invasive interfaces for people who use medical ventilators and other assistive technologies include masks, nasal pillows, and tubes. However existing interfaces have several disadvantages. Some interfaces cover parts of the face and may be uncomfortable or interfere with vision. Existing interfaces are also be difficult to position and adjust to make an air-tight seal, and require a mounting arm or bracket and/or complicated cleaning processes. Thus, there is a need for oral interfaces which are less bulky and obstructive, more comfortable, and allow enhanced exhalation and inhalation of gases or fluids.

SUMMARY

Provided are various systems and apparatus relating to oral interfaces. Various embodiments are described for an oral interface which provides improved functional aspects. In one aspect, which may include at least a portion of the subject matter of any of the preceding and/or following examples and aspects, a multipurpose oral interface is provided. The oral interface comprises a body comprising a flow channel extending through the body from a first opening to a second opening. The oral interface further comprises a lip commissure hook extending from a first end of the body in a curved configuration. The oral interface further comprises an intraoral portion extending from the lip commissure hook to form a gap between the intraoral portion and the body. The flow channel extends through the lip commissure hook and the intraoral portion to the first opening. The oral interface further comprises an outer mandibular contact extending from the body.

The intraoral portion and the outer mandibular contact may be configured to apply frictional forces against the user's mandible and cheek to stabilize the oral interface upon the user. The outer mandibular contact may be configured to rest against a first portion of the user's mandible located outside of the user's mouth. The outer mandible contact may be customized to conform to a shape of the first portion of the user's mandible. The outer mandibular contact may comprise a rubberized material to increase the frictional forces. The intraoral portion may further comprise an inner mandibular contact including a second surface configured to rest against a second portion of the user's mandible located within the user's mouth. The inner mandible contact may be customized to conform to a shape of the first portion of the user's mandible. The outer mandible contact may be integrated with the body such that the flow channel extends through the outer mandible contact.

The body may further comprise a connector portion extending from a second end of the body, the connector portion including the second opening interconnected with the flow channel. The second opening may be configured to be coupled to a ventilator hose or hose connector. The lip commissure hook may comprise a flattened surface configured to interface with the user's lips. The intraoral portion may comprise one or more additional openings interconnected with the flow channel. The oral interface may allow bidirectional flow of air through the flow channel from the first opening to the second opening.

The oral interface may comprise an elastically deformable flexible material. A force can be applied to an original state of the oral interface to elastically deform the oral interface to an elastically deformed state in order to mount the oral interface onto the first portion and the second portion of the user's mandible. Upon removal of the force, the oral interface returns to the original state to apply frictional forces against the user's mandible and cheek.

The oral interface may further comprise a bite stabilizer extending from the intraoral portion and positioned to interface with the user's teeth when worn. The oral interface may further comprise a switch coupled to the bite stabilizer, wherein the switch is configured to be positioned between the user's tongue and teeth when worn, wherein the switch is communicatively coupled to a user device.

Other implementations of this disclosure include corresponding devices, systems, and, as well as and associated methods for operating the described oral interfaces. These other implementations may each optionally include one or more of the following features. For instance, provided is a system comprising a ventilator and an oral interface coupled to the ventilator via a hose.

Also provided is a method for operating an oral interface. The method comprises positioning an intraoral portion of the oral interface against a first portion of a user's jaw located within the user's mouth. The oral interface comprises a body and a lip commissure hook extending from a first end of the body in a curved configuration, and the intraoral portion extends from the lip commissure hook to form a gap between the intraoral portion and the body. A flow channel extends through the body, the lip commissure hook, and the intraoral portion to a first opening. The method further comprises positioning an outer mandibular contact of the oral interface against a second portion of the user's jaw located outside the user's mouth. The outer mandibular contact extends from the body.

The method may further comprise applying a first force to an intraoral portion of the oral interface, and applying a second force to an outer mandibular contact. The second force is substantially opposite to the first force, and the first force and the second force cause the oral interface to elastically deform from an original state to an elastically deformed state. When the oral interface is in the elastically deformed state, the intraoral portion is positioned against the first portion of the user's jaw, and the outer mandibular contact is positioned against the second portion of the user's jaw. The method may further comprise releasing the first force and the second force to return the oral interface to the original state such that the intraoral portion and the outer mandibular contact apply frictional forces against the user's jaw and cheek to stabilize the oral interface upon the user.

These and other embodiments are described further below with reference to the figures.

BRIEF DESCRIPTION OF THE DRAWINGS

The disclosure may best be understood by reference to the following description taken in conjunction with the accompanying drawings, which illustrate particular embodiments of the present disclosure.

FIGS. 1A, 1B, 1C, 1D, and 1E illustrate various perspective views of an example of an oral interface, in accordance with one or more embodiments.

FIGS. 2A, 2B, and 2C illustrate various perspective views of an example of an oral interface with customized contact surfaces, in accordance with one or more embodiments.

FIGS. 5A, 5B, 5C, and 5D illustrate example oral interfaces with an integrated outer mandibular contact worn by a user, in accordance with one or more embodiments.

FIGS. 7A, 7B, 7C, 7D, 7E, 7F, 7G, and 7H illustrate an example oral interface comprising additional modified structures, in accordance with one or more embodiments.

FIGS. 8A, 8B, and 8C illustrate another example oral interface with a modified intraoral portion, in accordance with one or more embodiments.

DETAILED DESCRIPTION

Figure 1E:
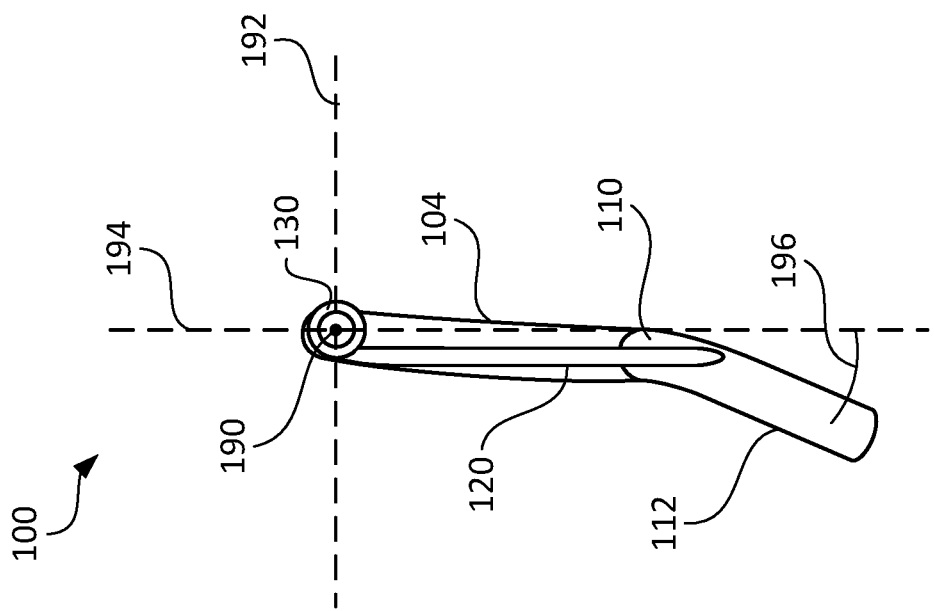

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting. On the contrary, it is intended to cover alternatives, modifications, and equivalents as may be included within the spirit and scope of the present disclosure as defined by the appended claims.

For example, the techniques of the present disclosure will be described in the context of particular apparatus, such as medical ventilator, suction, or sip-and-puff devices. However, it should be noted that the techniques and mechanisms of the present disclosure apply to various other devices requiring pneumatic interaction with a user. In the following description, numerous specific details are set forth in order to provide a thorough understanding of the present disclosure. Particular example embodiments of the present disclosure may be implemented without some or all of these specific details. In other instances, well known process operations have not been described in detail in order not to unnecessarily obscure the present disclosure. Various techniques and mechanisms of the present disclosure will sometimes be described in singular form for clarity. However, it should be noted that some embodiments include multiple iterations of a technique or multiple instantiations of a mechanism unless noted otherwise.

Overview

The present disclosure describes an improved oral interface which may be implemented with various systems and for various functions. According to various embodiments, the oral interfaces described herein may be multipurpose pneumatic oral interfaces (MPOI) which may be implemented with various breathing apparatus or assistive technology systems. For example, an example oral interface may be used in conjunction with a medical ventilator system to allow improved intake or exchange of air. As another example, an oral interface presented herein may be used as a user interface for a sip-and-puff (SNP) device to send signals by using air pressure by "sipping" (inhaling) or "puffing" (exhaling) through the oral interface. In yet another example, an oral interface presented herein may be used with a medical suction pump for suctioning fluid out of a user's mouth.

The described oral interfaces provide improved attachment capabilities for the user for more convenient and continual operation. In various embodiments, the oral interface comprises a substantially vertical tubular body or shaft with a flow channel. A lip commissure hook extends upward from the body and curves toward the user to form a hook structure configured to interface with the lips, and particularly the lip commissure, of the user. An intraoral portion then extends from the lip commissure hook and is configured to be positioned substantially in the user's mouth. The intraoral portion may comprise an inner mandible contact configured to rest against portions of the user's mandible within one side of the user's mouth, such as the gingiva, teeth, and/or inner cheek. The flow channel is continuous and extends from the body through the lip commissure hook and intraoral portion to a first opening. The flow channel is also continuous and extends from the body to a second opening at a connector portion which is configured to couple to a tube for transfer of gases or fluids. The oral interface may further comprise an outer mandible contact configured to rest against portions of the user's mandible outside of the user's mouth, such as the chin, jaw, and/or cheek, on the same side as the inner mandible contact.

In certain embodiments, the outer mandible contact is integrated with the body such that the flow channel is continuous and extends from the body through the outer mandible contact to the second opening at the end of the connector portion. The inner and outer mandible contacts may include customized surfaces to more securely and comfortably sit against respective portions of the user's body. Additional openings may be positioned on the intraoral portion to ensure unrestricted flow into and out of the mouth, as well as soften the flow pressure of gases and fluids into the mouth.

In particular embodiments, the lip commissure hook may comprise additional features or be shaped to enhance the fit and operation of the oral interface. For example, the lip commissure hook may be flattened to enhance comfort, as well as improve the seal created between the lips and the lip commissure hook. As such, loss of suction or loss of output of gases or fluids is reduced or eliminated. The flattened surface of the lip commissure hook may additionally be angled or contoured to match the shape of the user's lips near the anatomical lip commissure. The lip commissure hook may also be configured with a lip guard which may also comprise curved surfaces to improve the interface with the user's lips and enhance the seal during suction.

Additional stabilization features include a bite stabilizer which may extend from the lip commissure hook and/or the intraoral portion. The bite stabilizer is positioned between and along the upper and lower teeth of the user so that the user may bite down and stabilize the oral interface during operation. The bite stabilizer may further comprise edges which may clip or couple the bite stabilizer to the bottom or top row of teeth of the user. The bite stabilizer may further be configured with an input device with a switch or joystick which may be operated by the user's tongue, teeth, lips, cheek, chin or other part of their face or mouth, thereby combining the functionality of gas/fluid exchange with device control.

The above features provide for a lightweight oral interface that may be continuously worn by a user. Existing oral interfaces or mouthpieces are typically positioned near the user's mouth and must be input into the mouth by the user each time use is desired. As such, the user must lean, tilt, or otherwise move their head to grasp the mouthpiece each time. Other oral interfaces are bulky and/or are attached to various other portions of the user's head, such as the ears, forehead, etc. The described oral interfaces address many of these disadvantages of existing devices by including less material to reduce bulk and enhance the comfort and stability so that the oral interface may be easily inserted in the mouth and worn continuously such that the oral interface may be used without interruption or extra effort, and without interfering with vision or obstructing the face. The configuration of the provided oral interface also promotes the formation of an airtight seal between the user's lips. The oral interface also stays in place requiring minimal adjustment and do not require a mounting arm or bracket.

Example Embodiments

Figure 1D:
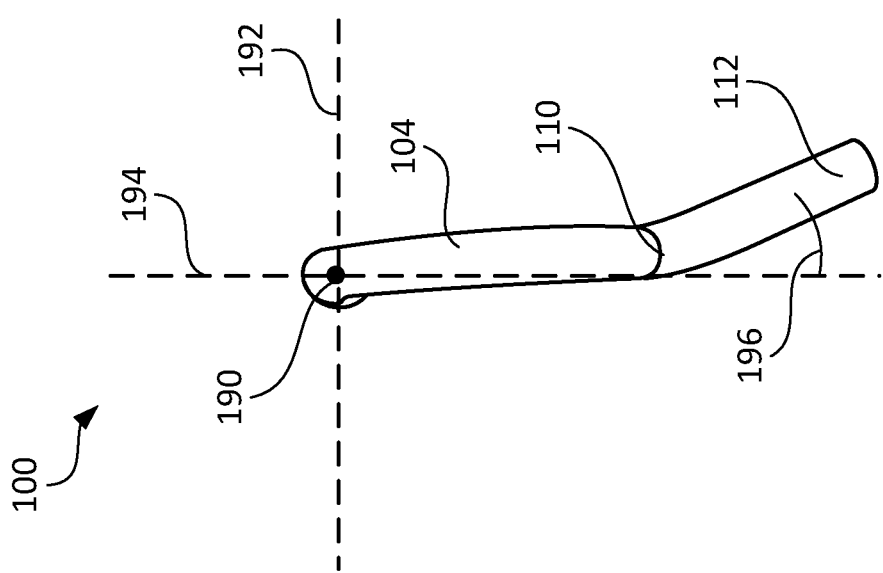

With reference to FIGS. 1A-1E, shown are various perspective views of an example oral interface 100, in accordance with one or more embodiments. FIG. 1A illustrates a left side view of oral interface 100, FIG. 1B illustrates a front view of oral interface 100, FIG. 1C illustrates a right side view of oral interface 100, FIG. 1D illustrates a top view of oral interface 100, and FIG. 1E illustrates a bottom view of oral interface 100. In various embodiments, an example oral interface 100 comprises body 102, lip commissure hook 104, intraoral portion 110, inner mandible contact 112, outer mandible contact 120, and connector portion 130. The various components or portions of oral interface 100 are separated in FIGS. 1A-1C by dashed lines for illustrative purposes.

Body 102 may comprise an elongated tubular structure with a hollow passageway or flow channel. In various embodiments, body 102 and the flow channel may include various geometric configurations. As shown in FIGS. 1A-1C, body 102 includes a cylindrical pipe structure with a circular cross-section. Vertical axis 190 runs through the center of body 102. However, it should be recognized that body 102 may be configured with various cross-sectional geometries, including ovals, rectangles, and other polygons. The body of various example oral interfaces may be described with reference to an upper end and a lower end of the structure. Other components or portions of example oral interfaces may be described with reference to a proximal end that is positioned relatively closer to the main body and a distal end that is positioned relatively further from the main body.

In various embodiments, oral interface 100 further comprises lip commissure hook 104 extending from an upper end (or "first end") of main body 102 in a curved configuration. Lip commissure hook 104 may extend upward from the upper end of main body 102 and curve toward the front face of oral interface 100 to form a hook shape. At least a portion of lip commissure hook 104 may be configured to contact the lip commissure of a user, as will be further described below. Intraoral portion 110 extends from the distal end of lip commissure hook 104 to form a hook-like structure with gap 150 between intraoral portion 110 and body 102. Gap 150 is a substantially horizontal space and may be analogous to the gap or gape of a hook between the hook point and the hook shaft. As such gap 150 may be referred to herein as gape 150. In particular embodiments, gap 150 may be 1 inch to 2.5 inches wide. However, the size of gap 150 may be varied or customized to fit a particular user's mouth.

Intraoral portion 110 may extend from the distal end of lip commissure hook 104 to a first opening 142. First opening 142 may be referred to herein as an intraoral opening. The flow channel may be continuous and extend from the main body through lip commissure hook 104 and intraoral portion 110, to intraoral opening 142. In some embodiments, intraoral portion may extend relatively vertically downward from the distal end of lip commissure hook 104 and may form an additional portion of the hook structure of oral interface 100. In some embodiments, a portion of intraoral portion 110 may be configured as an inner mandible contact 112 which comprises a contact surface 113 for contacting one or more portions of the mandible of a user within the user's mouth. Contact surface 113 may comprise at least a portion of inner mandible contact 112. As shown in FIGS. 1A-1C, contact surface 113 is substantially located on the left side of inner mandible contact 112. In various embodiments, contact surface 113 of inner mandible contact 112 may contact the teeth and/or gums (gingiva) of the user. Portions of intraoral portions 110 may also be configured to contact the inner cheek of the user.

In some embodiments, intraoral portion 110 may be configured at an angular orientation relative to main body 102 and/or other portions of oral interface 100. This angular orientation may be shown with respect to FIGS. 1D and 1E. Lateral axis 192 and horizontal axis 194 are shown in relation to vertical axis 190. Axes 190, 192, and 194 are perpendicular axes. As shown, intraoral portion 110 may be offset relative to the lip commissure hook 104 such that the inner mandible contact 112 is positioned away from horizontal axis at angle 196. This angular orientation may be more suitable to the geometry of the mouth of a user. For example, the angular orientation of the oral interface may match the angular orientation or shape of the user's teeth or gums when worn by the user.

In various embodiments, oral interface 100 further comprises outer mandible contact 120 extending from main body 102 toward the front of oral interface 100. A contact surface 121 of outer mandible contact 120 may be configured to contact a portion of the user's mandible outside of the user's mouth. For example, contact surface 121 of outer mandible contact 120 may rest against various portions of a user's chin, jawline, and/or cheek. As shown in FIGS. 1A-1C, contact surface 121 is substantially located on the left side of outer mandible contact 120.

Gap 152 may be formed between outer mandible contact 120 and intraoral portion 110. More specifically, gap 152 exists between outer mandible contact 120 and inner mandible contact 112. In particular embodiments, gap 152 may be approximately 0.25 inches to 1 inch wide However, the size of gap 150 may be varied or customized to fit a particular user's face. As shown in FIGS. 1B and 1E, outer mandible contact 120 and intraoral portion 110 are substantially aligned along horizontal axis 194. As such, gap 152 is a substantially vertical space. However, outer mandible contact 120 may be offset from horizontal axis 194 to fit the user's face. In some embodiments, outer mandible contact 120 may comprise a malleable material, such as metal, which can be bent to multiple desired positions relative to horizontal axis 194 or to intraoral portion 110. The malleable material may be surrounded a plastic or rubberized coating. A plastic or rubberized coating may increase friction against the user's chin, jaw, and/or cheek to increase stability while in use.

In other embodiments, an oral interface may comprise an elastically deformable material. In such embodiments, the oral interface may be manipulated from an original state (shown in FIGS. 1A-1E) into an elastically deformed state by applying forces to various portions. The oral interface may then return to return to the original state upon release of the forces. In some embodiments, the oral interface may comprise various materials which provide desired characteristics, such as rigidity, flexibility, and strength. Such materials may include various thermoplastics or resins, such as photopolymer resins or dental resins, which may be compatible with 3D printing manufacturing processes. Such resins may be medical or food grade.

The oral interface depicted in FIGS. 1A-1E may be configured to be worn or attached to the right side of a user's face. Oral interface 100 and the other examples provided herein will be described as configured to be worn or attached to the right side of a user's face where applicable. However, it should be understood that the oral interfaces described herein may be configured to worn or attached to the left side or other portions of the user's face. An oral interface configured to be worn or attached to the opposite side of a user's face would comprise a mirror image of the oral interfaces described herein. For example, an oral interface configured to attach to the left side of a user's face may comprise contact surfaces 113 and 121 on opposite sides of the corresponding structures 112 and 120, respectively. Similarly, an oral interface configured to attach to the left side of a user's face may additionally comprise an intraoral portion 110 with an opposite angular orientation from the horizontal axis.

Body 102 may further comprise connector portion 130 extending from the lower end of main body 102. In other words, connector portion 130 may extend from the lower end of main body 102 from a proximal end to a distal end. The distal end of connector portion 130 may comprise a second opening 144 that is interconnected with the flow channel. In various embodiments, connector portion 130 may be configured to interface with a connector (such as connector 132-A in FIG. 1A or 132-B in FIG. 1B) that couples the oral interface to a tube or other component of a device, such as a medical ventilator or SNP apparatus. In some embodiments, a connector, such as connector 132-A, is a separate component coupled to connector portion 130. In some embodiments, a connector, such as connector 132-B, is an integral component of connector portion 130. In such embodiments, second opening 144 may be located at the distal end of the connector. FIG. 1C illustrates an embodiment without any connector attached to connector portion 130.

In various embodiments, various portions of the oral interface may be customized to fit a particular user. With reference to FIGS. 2A-2C, shown are various perspective views of another example oral interface 200 with customized contact surfaces, in accordance with one or more embodiments. FIG. 2A illustrates a left side view of oral interface 200, FIG. 2B illustrates a front view of oral interface 200, and FIG. 2C illustrates a right side view of oral interface 200. In various embodiments, oral interface 200 may comprise similar components as oral interface 100, including main body 102, lip commissure hook 104, intraoral portion 110, and connector portion 130.

However, oral interface 200 may comprise a customized inner mandible contact 212 and customized outer mandible contact 220. Customized inner mandible contact 212 comprises contact surface 213 which is modified with a geometry conforming to the surface of the user's teeth and/or gums on the appropriate side of the user's face. Similarly customized outer mandible contact 220 comprises contact surface 221 which is modified with a geometry conforming to the surface of the user's chin, jawline, or cheek on the appropriate side of the user's face.

Figure 3B:
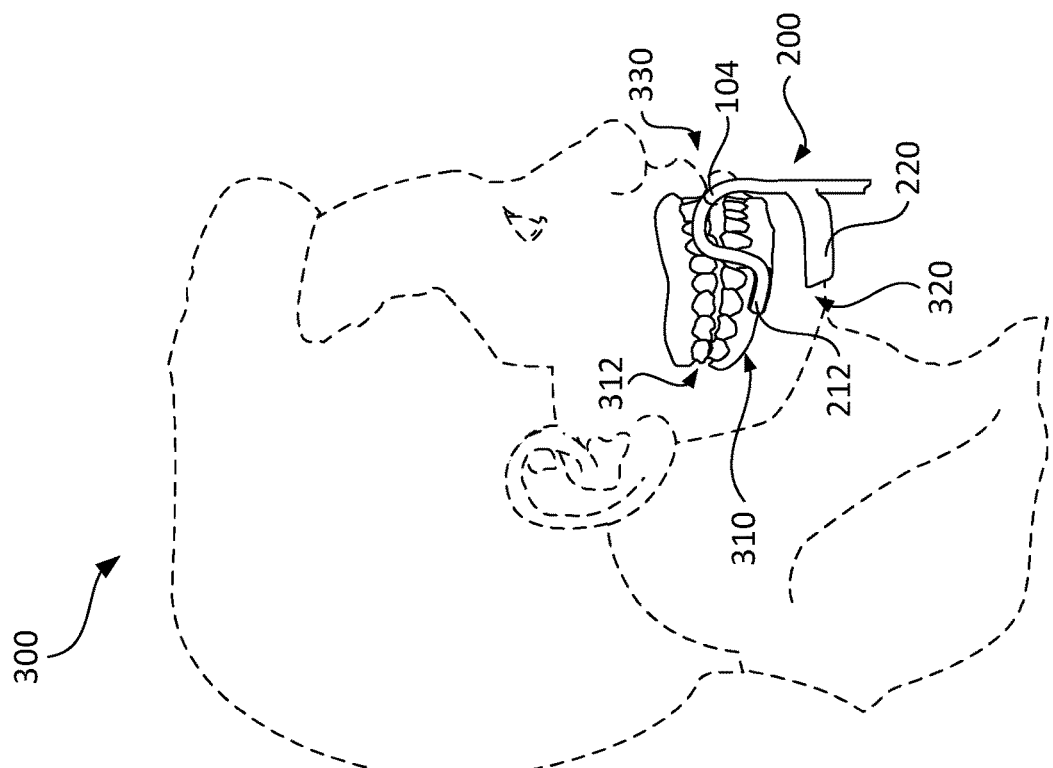
FIGS. 3A and 3B illustrate an example oral interface worn by a user, in accordance with one or more embodiments.
Figure 3A:
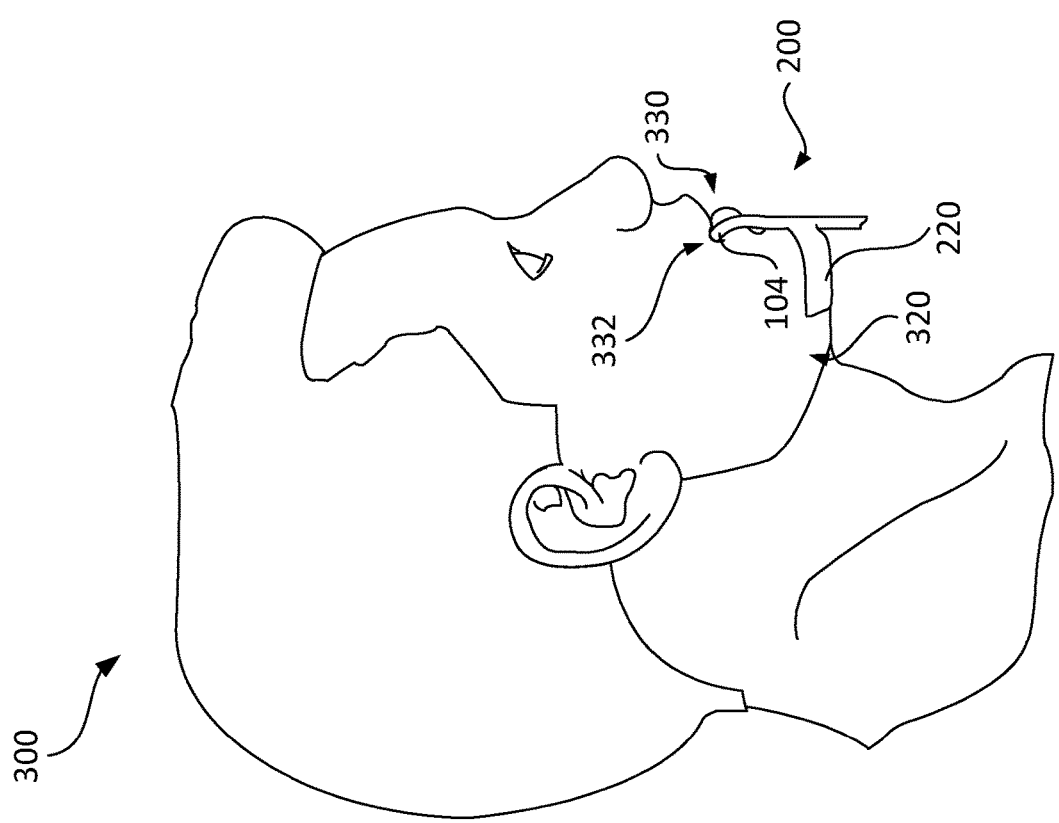

FIGS. 3A and 3B illustrate example oral interface 200 worn by a user 300, in accordance with one or more embodiments. As illustrated, user 300 comprise lips 330 with lip commissure 332 corresponding to the corner of the mouth, where the vermillion border of the superior labium (upper lip) meets that of the inferior labium (lower lip). Lip commissure hook 104 may rest against the side of the mouth at the lip commissure 332. User 300 further comprises outer mandible 320 or which may comprise at least a portion of the external surface of the user's chin, jaw, and/or cheek. As shown, customized outer mandible contact 220 is in contact with outer mandible 320. As illustrated in FIG. 3B, user 300 further comprises inner mandible 310, which may comprise portions of the user's gums (gingiva) and/or teeth 312. As shown, customized inner mandible contact 212 is in contact and interfaces with inner mandible 310.

Figure 4A:
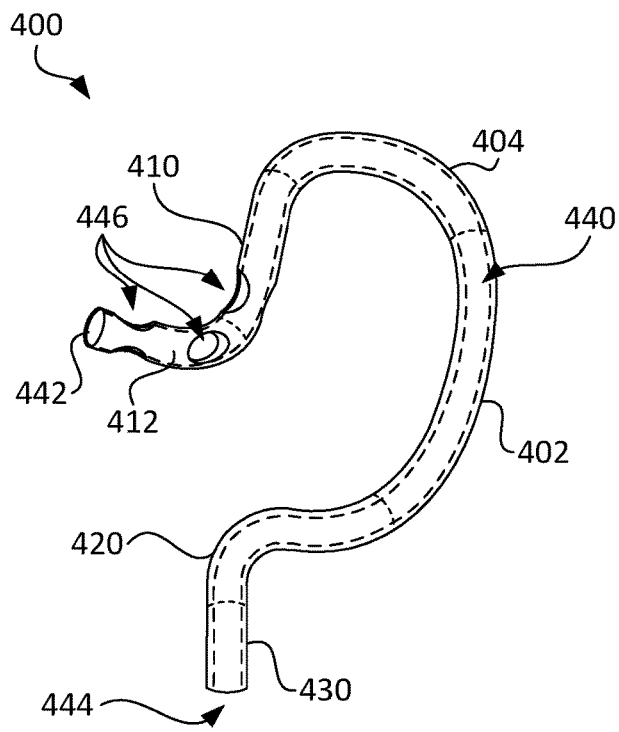
FIGS. 4A, 4B, 4C, 4D, 4E, 4F illustrate various perspective views of an example of an oral interface with an integrated outer mandibular contact, in accordance with one or more embodiments.
Figure 4B:
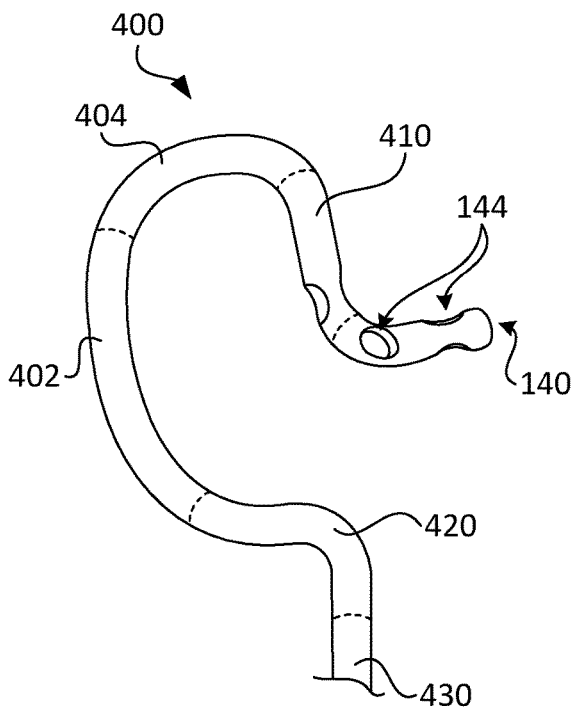
Figure 4C:
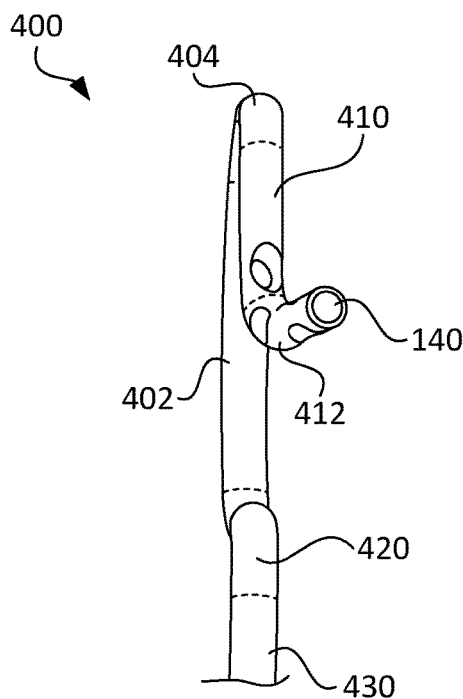
Figure 4D:
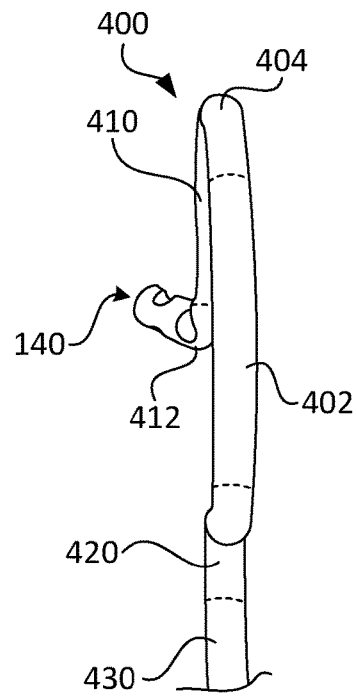

In various embodiments, the outer mandible contact may be integrated with the main body of the oral interface. With reference to FIGS. 4A-4D, shown are various perspective views of another example oral interface 400 with an integrated outer mandible contact, in accordance with one or more embodiments. FIG. 4A illustrates a right side view of oral interface 400, FIG. 4B illustrates a left side view of oral interface 400, FIG. 1C illustrates a front view of oral interface 400. FIG. 4D illustrates a back view of oral interface 400. Oral interface 400 comprises main body 402, lip commissure hook 404, intraoral portion 410, inner mandible contact 412, and connector portion 430, similar to analogous portions and components in the previously described examples. Oral interface further comprises an integrated outer mandible contact 420. Flow channel 440 in the interior is shown in dashed lines and extends through the portions of oral interface 400 from first opening 442 to second opening 444.

In various embodiments, outer mandibular contact 420 may be integrated with main body 402. As such, a proximal end of outer mandibular contact 420 may extend from the lower end of main body 402 to a distal end of the outer mandibular contact 420. Connector portion 430 of the oral interface may then extend from the distal end of outer mandibular contact 420. The flow channel may extend continuously through outer mandibular contact 420 to the second opening 444 at the distal end of connector portion 430. It should be understood that connector portion 430 may comprise any of the configurations of connector portions described above.

Such configuration incorporating an integrated outer mandibular contact reduces the amount of material forming the oral interface. As such this may reduce the amount of material and, in turn, manufacturing costs of the oral interface. Additionally, reducing the amount of material may improve the comfort to the user by reducing the weight of the oral interface, as well as providing a smaller contact surface against the outer mandible of the user.

In some embodiments, the intraoral portion may be configured with additional openings. As shown in FIGS. 4A-4D, intraoral portion 410 comprises additional openings 446 in addition to first opening 442. Some additional openings 446 are located on the inner mandible contact 412 of intraoral portion 410. Although six additional openings 446 are illustrated, it should be recognized that an oral interface may be configured with any number of additional openings. In some instances, one or more openings may be completely or partially blocked by various portions of the user's mouth, such as by the gums, teeth, or inner cheek. Thus, the additional openings 446 ensure that there are adequate unrestricted passageways for air or fluid to flow into the user's mouth. Multiple additional openings 446 may also dampen the pressure of air or fluid entering the user's mouth by increasing the spreading the pressure of a given flow rate amongst multiple openings. This may provide a more comfortable experience for the user during operation.

Figure 4F:
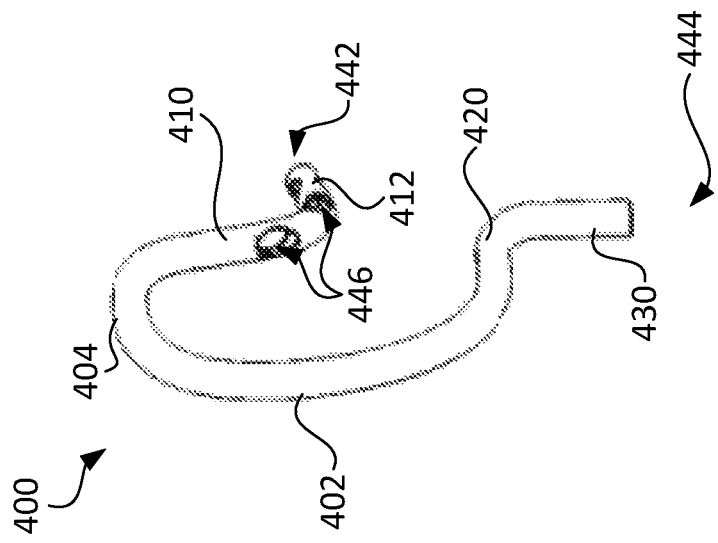
Figure 4E:
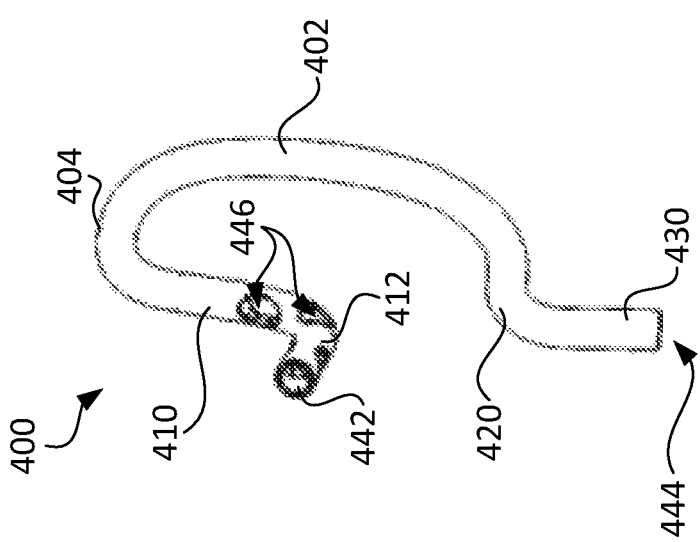
Figure 5D:
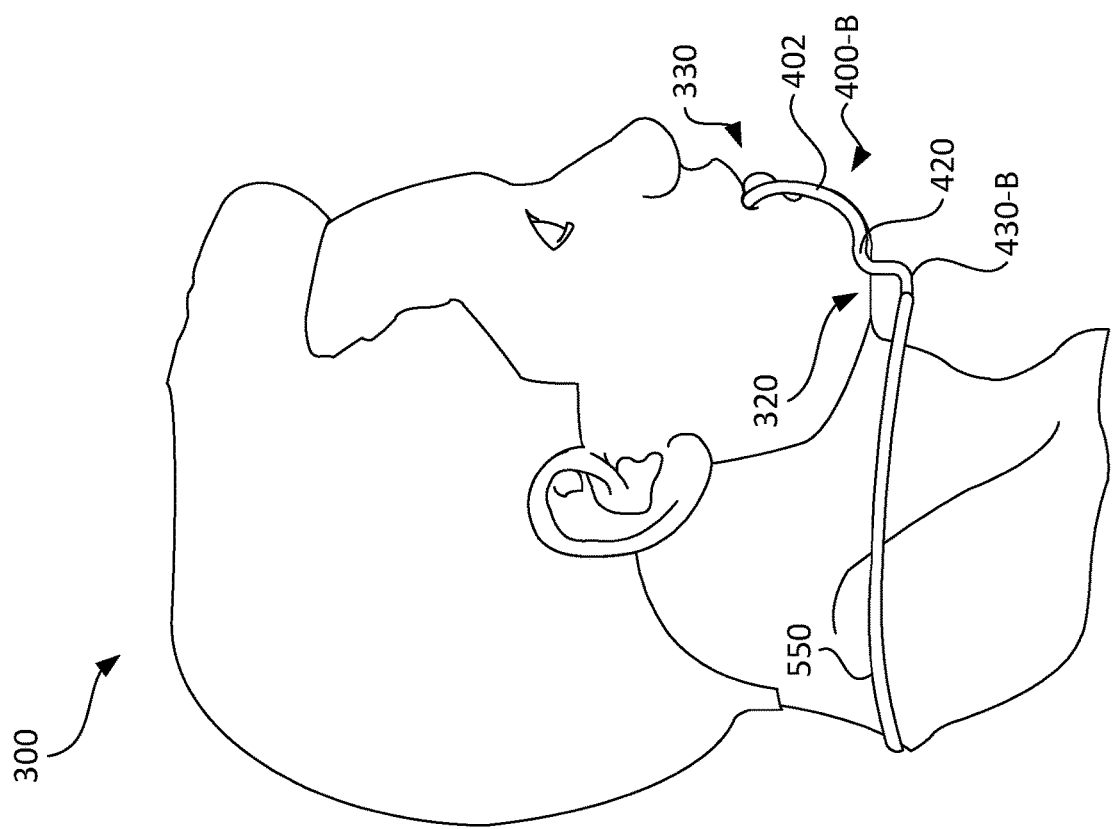

FIGS. 4E and 4F illustrate additional perspective views of oral interface 400. FIG. 4E illustrates a front right perspective view of oral interface 400, and FIG. 4F illustrates a back left perspective view of oral interface 400. FIGS. 5A, 5B, 5C, and 5D illustrate example oral interfaces with an integrated outer mandibular contact worn by a user, in accordance with one or more embodiments. FIGS. 5A and 5B illustrate example oral interface 400 worn by user 300, in accordance with one or more embodiments. As shown, oral interface 400 may be similarly worn as oral interface 200 in FIGS. 3A and 3B. As further illustrated, the integrated outer mandible contact 420 extends from the main body toward the user and contacts the outer mandible 320 of user 300.

Figure 5C:
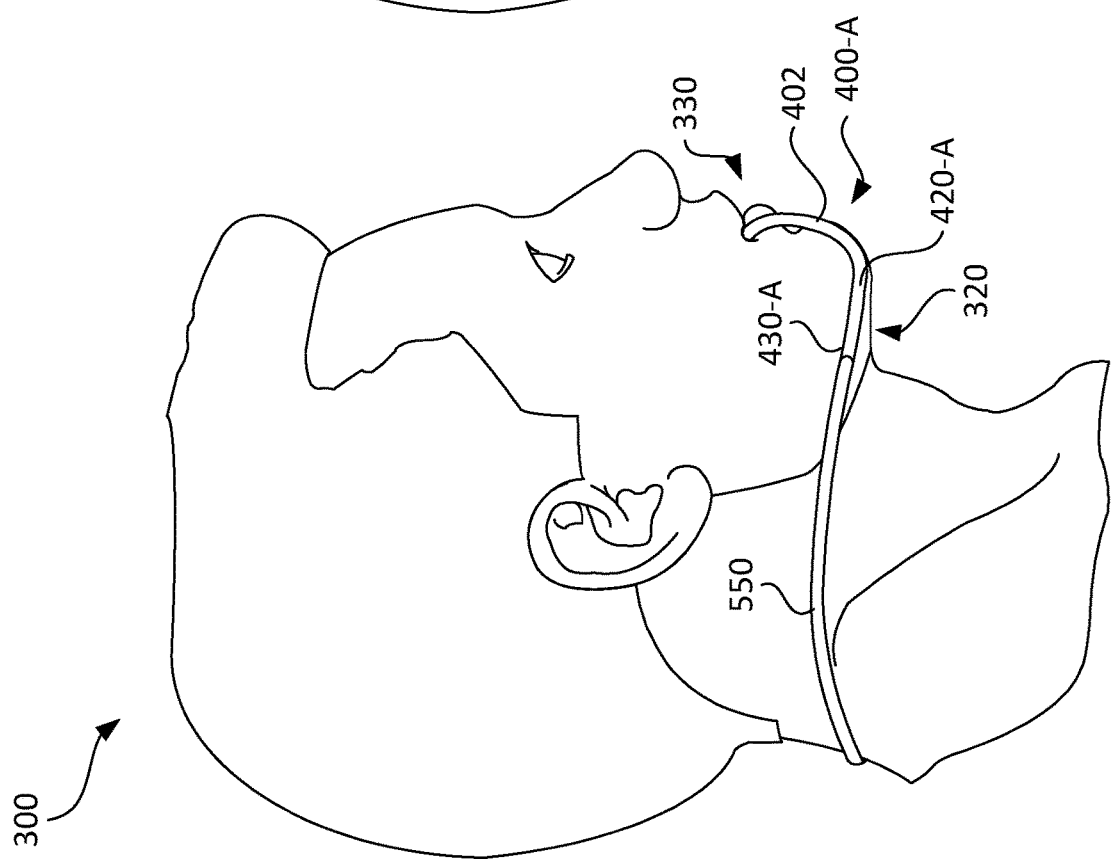

In some embodiments, an integrated outer mandible contact is configured to extend toward the back of the user's head. FIGS. 5C and 5D illustrate additional example oral interfaces with integrated outer mandible contacts worn by a user, in accordance with one or more embodiments. FIG. 5C shows oral interface 400-A with an integrated outer mandible contact 420-A which does not curve back downward as outer mandible contact 420 of oral interface 400 does. This may result in a more comfortable attachment for the user by providing additional contact surface against the user's outer mandible 320. Additional customized surfaces may be applied to outer mandible contact 420-A. As such, the connector portion 430-A of oral interface 400-A is positioned horizontally with the second opening facing toward the back of the user. This configuration allows for a flexible tube 550 to be more easily positioned around the user's neck.

FIG. 5D shows oral interface 400-B, which comprises a similar outer mandible contact 420 to oral interface 400. Oral interface 400-B further comprises a connector portion 430-B which curves horizontally from outer mandible contact 420 toward the back of the user's head. As such, connector portion 430-B is positioned horizontally like connector portion 430-A with the second opening facing toward the back of the user. This similarly allows a flexible tube 550 to be more easily positioned around the neck of a user, without adding to the amount of contact area between outer mandible contact 420 and the user's outer mandible 320.

Figure 6C:
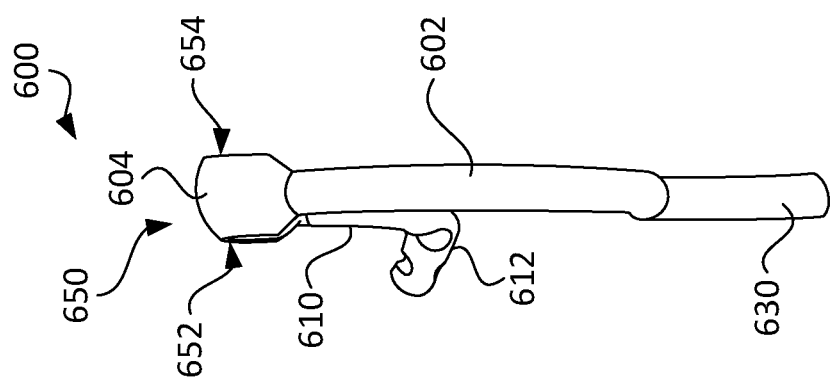
FIGS. 6A, 6B, 6C, 6D, and 6E illustrate an example oral interface comprising a flattened lip commissure hook, in accordance with one or more embodiments.
Figure 6B:
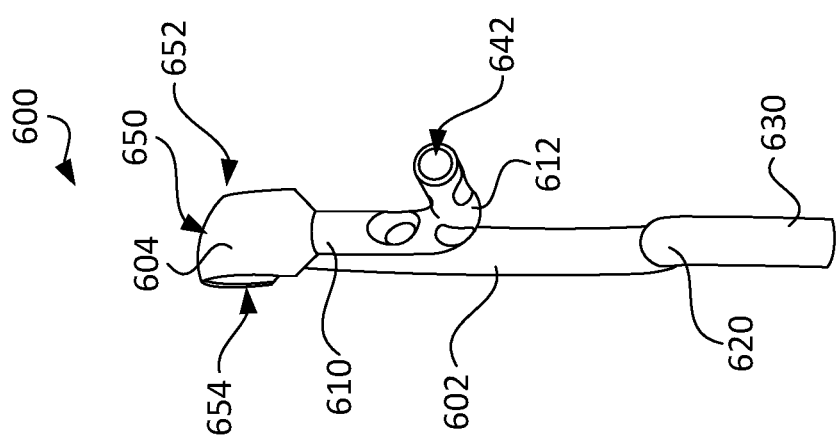
Figure 6A:
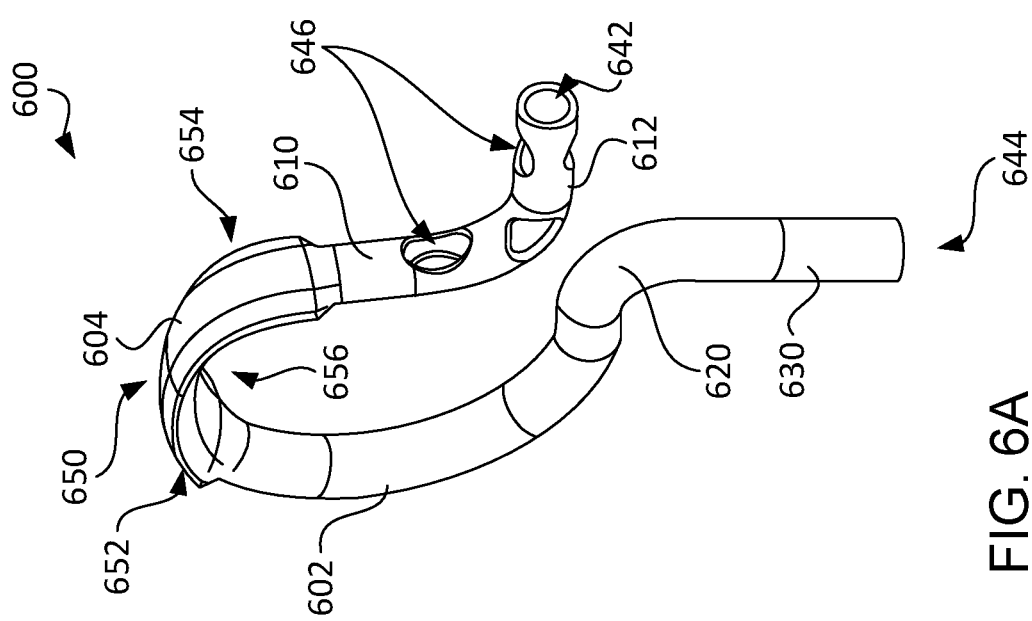
Figure 6E:
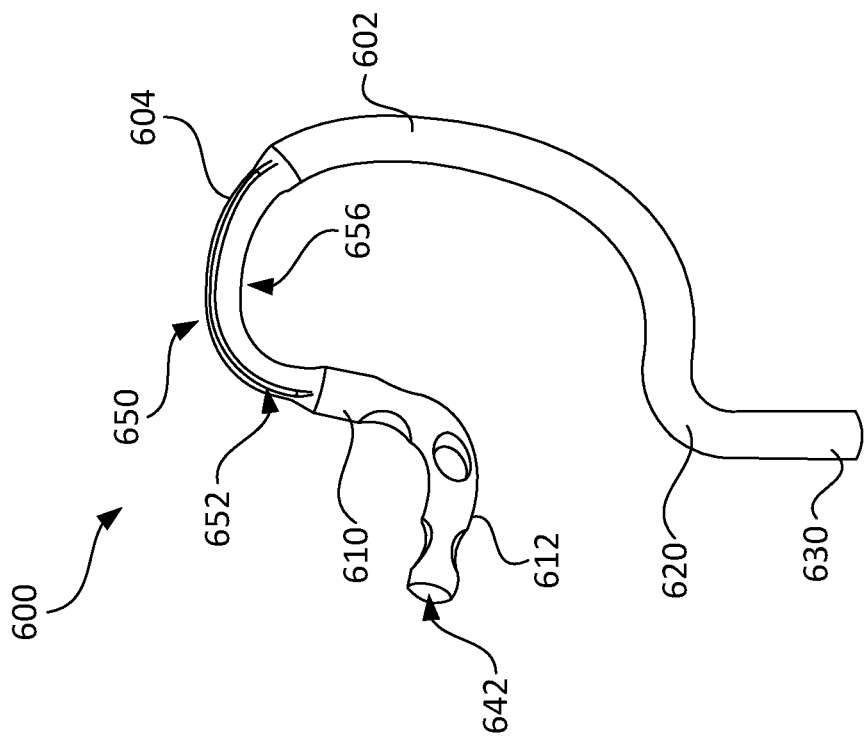
Figure 6D:
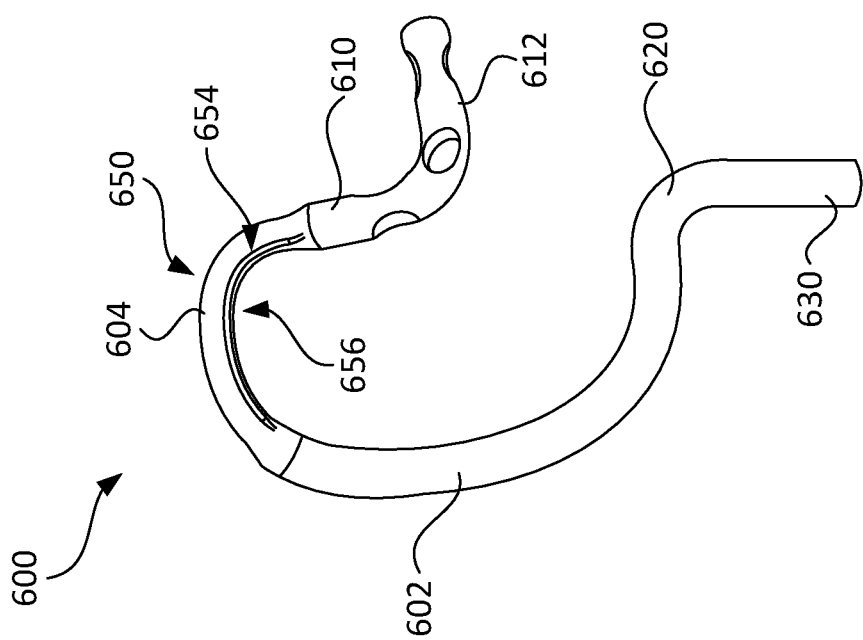

FIGS. 6A, 6B, 6C, 6D, and 6E illustrate an example oral interface 600 comprising a flattened lip commissure hook, in accordance with one or more embodiments. FIG. 6A illustrates a perspective view of oral interface 600, FIG. 6B illustrates a front view of oral interface 600, FIG. 6C illustrates a back view of oral interface 600, FIG. 6D illustrates a left side view of oral interface 600, and FIG. 6E illustrates a right side view of oral interface 600. As shown, oral interface 600 comprises main body 602 extending to outer mandible contact 620 and connector portion 630 with second opening 644, similar to analogous portions and components in the previously described examples. Although oral interface 600 is shown with an integrated outer mandible contact 620, it should be understood that oral interface 600 may instead comprise any one of the outer mandible contact embodiments described herein or no outer mandible contact at all. Oral interface 600 further comprises lip commissure hook 604 extending to intraoral portion 610 with inner mandible contact 612 and first opening 642. In some embodiments, oral interface 600 may also comprise one or more additional openings 646.

As shown, lip commissure hook 604 is flattened to comprise a broadened and flattened upper surface 650 and lower surface 656. The flattening of lip commissure hook 604 also results in right edge 652 and left edge 654. A flattened lip commissure hook may improve the comfort to the user while in operation. A flattened lip commissure hook also enhances the seal made between the user's lips 330 to improve intake or output of air or fluids. In some embodiments, the flattened surfaces 650 and 656 may be angled to conform to the curvature of the user's lips to improve comfort to the user, as well as to enhance to seal formed between the lips 330 and the lip commissure hook 604. In various embodiments, the angle of the flattened lip commissure hook 604 may be customized to conform to the shape of a particular user's lips. As shown left edge 654 is positioned higher than right edge 652. However, for another user, left edge 654 may be configured at the same height or lower than right edge 652.

Because of the flattened geometry of lip commissure hook 604, the flow channel at that portion of the oral interface may also be flattened. However, the flow channel at the lip commissure hook 604 may also be widened along with the geometry of the flattened lip commissure hook. As such, narrowing of the total cross-sectional area of the flow channel may be reduced or eliminated to maintain a suitable flow rate of air or fluids.

Figure 7A:
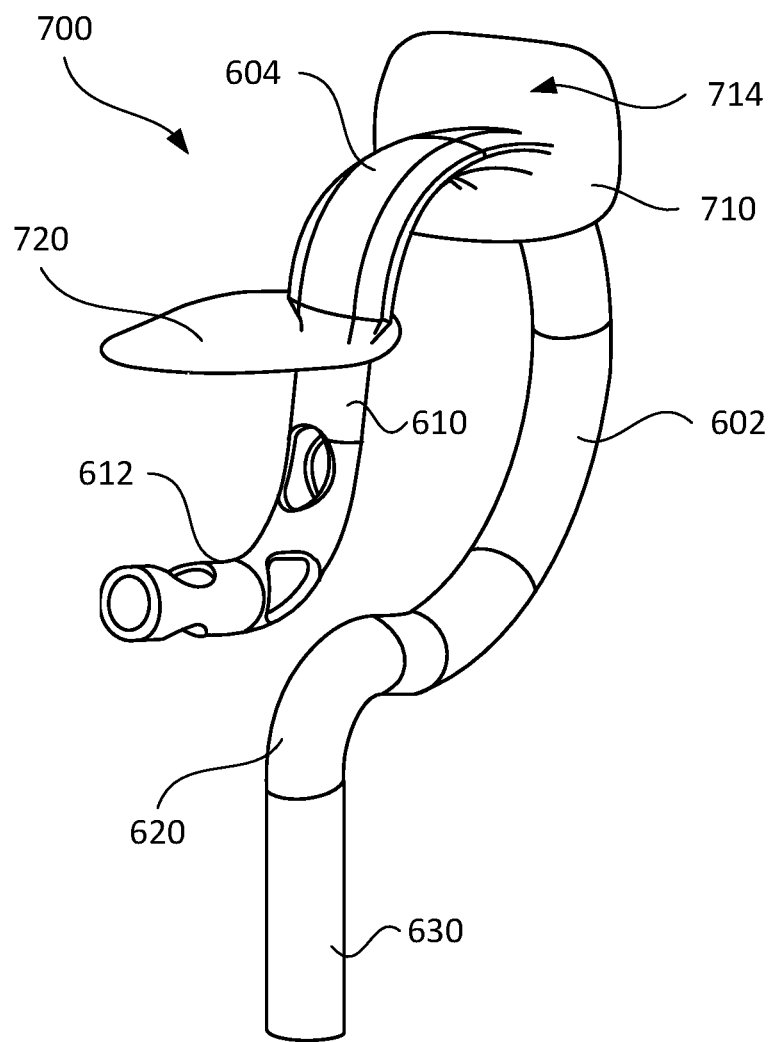
Figure 7C:
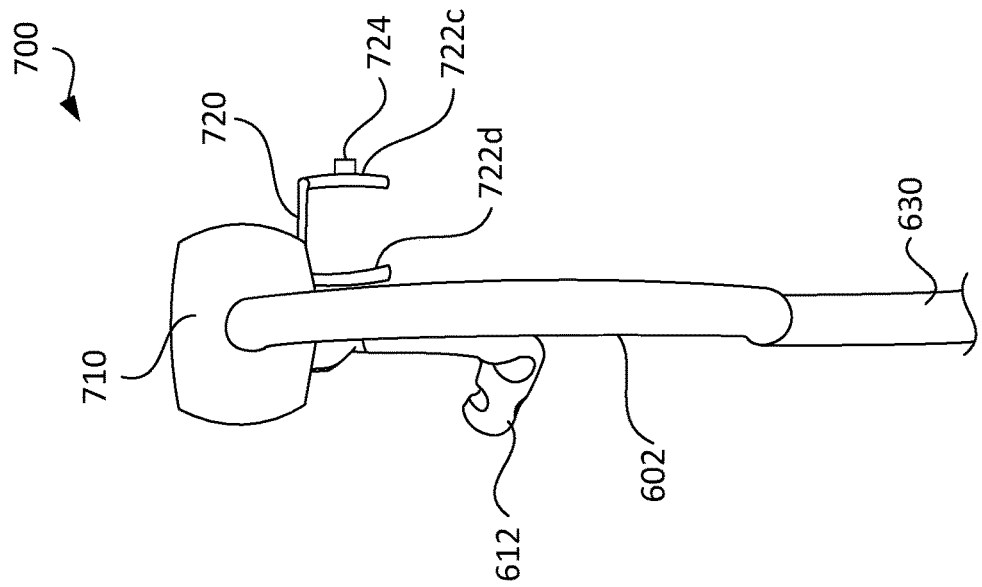
Figure 7B:
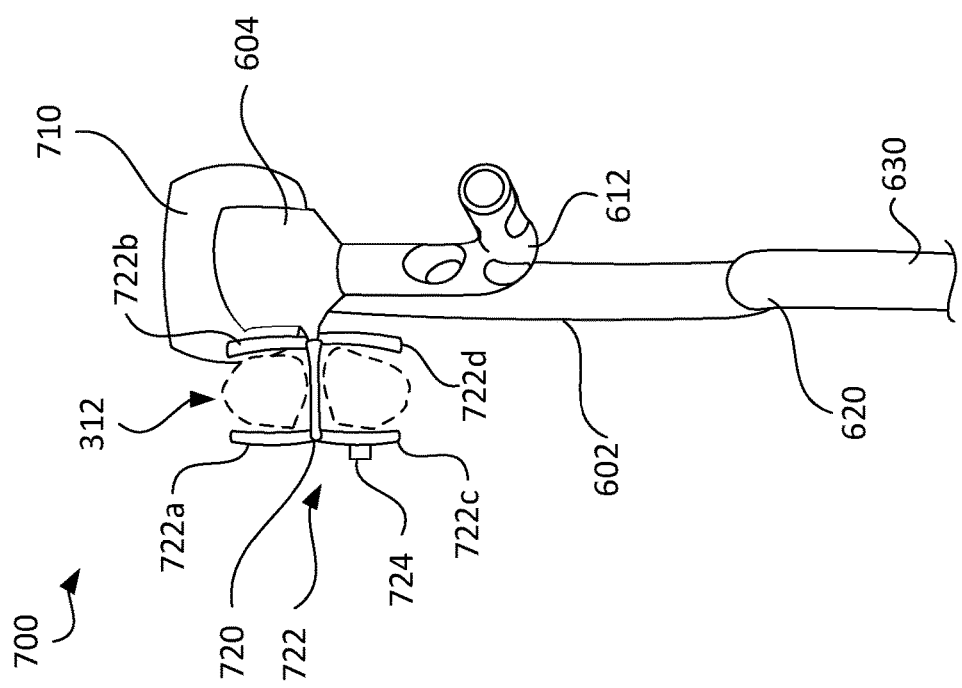
Figure 7E:
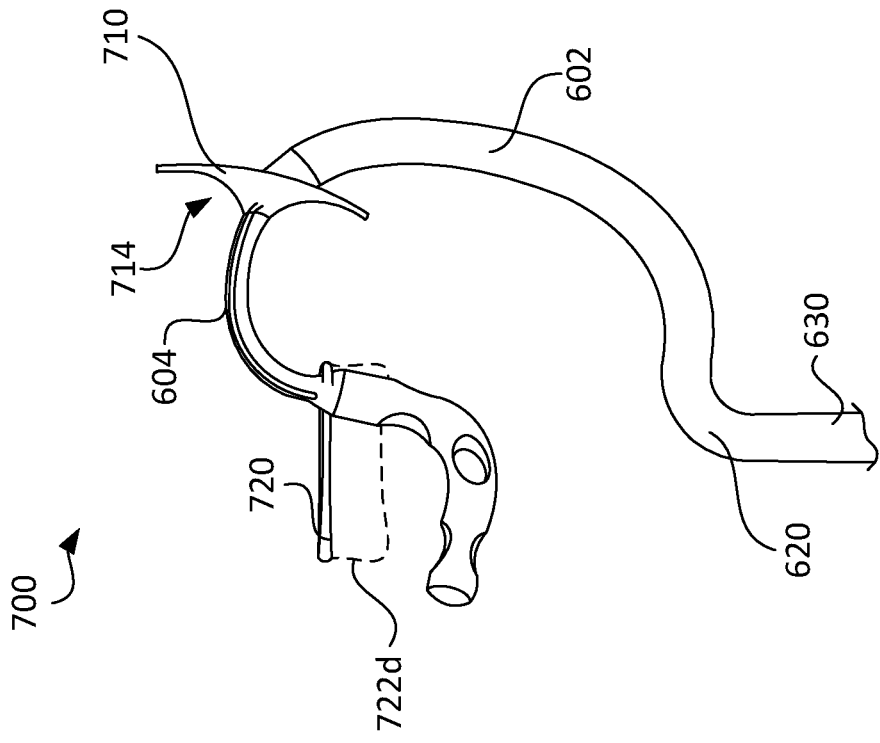
Figure 7D:
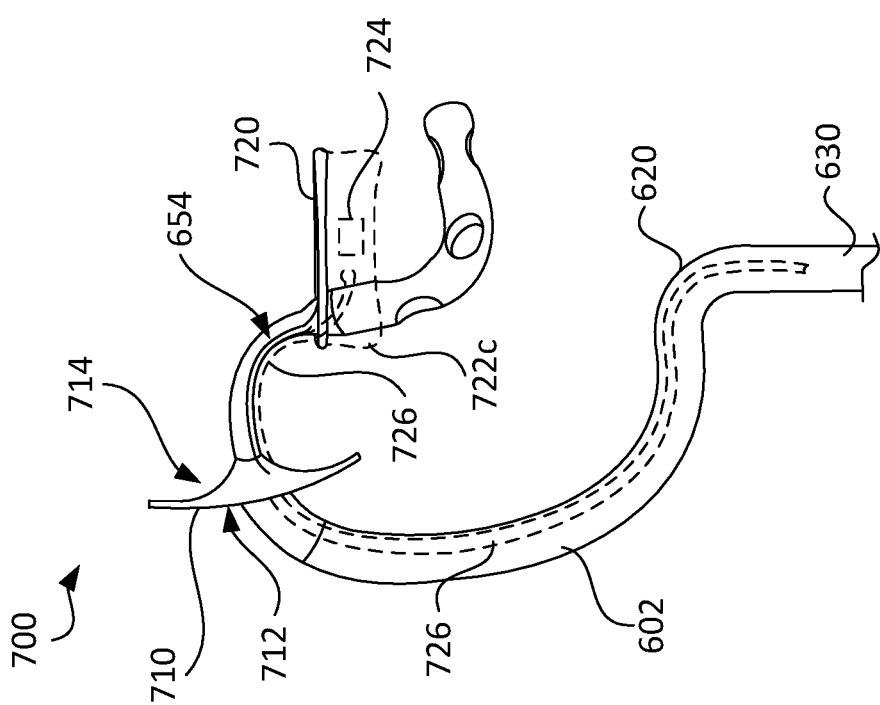

FIGS. 7A-7F illustrate an example oral interface 700 comprising additional modified structures, in accordance with one or more embodiments. FIG. 7A illustrates a perspective view of oral interface 700, FIG. 7B illustrates a front view of oral interface 700, FIG. 7C illustrates a back view of oral interface 700, FIG. 7D illustrates a left side view of oral interface 700, FIG. 7E illustrates a right side view of oral interface 700, and FIG. 7F illustrates a top view of oral interface 700. As shown, in various embodiments, example oral interface 700 includes similar or analogous features and components as oral interface 600, including main body 602, flattened lip commissure hook 604, intraoral portion 610 with inner mandible contact 612, outer mandible contact 620, and connector portion 630. Oral interface 700 may be further configured with lip guard 710 and bite stabilizer 720. Although oral interface 700 is shown with an integrated outer mandible contact 620, it should be understood that oral interface 700 may instead comprise any one of the outer mandible contact embodiments described herein or no outer mandible contact at all.

In various embodiments, lip guard 710 may be positioned around and/or extend from lip commissure hook 604. In some embodiments lip commissure hook 604 may be flattened as previously described. However, in other embodiments, lip guard 710 may be implemented with an unflattened, or substantially round lip commissure hook. As shown in FIGS. 7D and 7E, lip guard 710 may comprise a back surface 712 and front surface 714. In various embodiments, front surface 714 interfaces with lips 330 of user 300. The upper and lower portions of front surface 714 may comprise a curved surface which may conform to the contour of the user's lips to improve comfort and seal creation between the lips during suction by blocking any potential openings between the lips and lip commissure hook 604.

In various embodiments, bite stabilizer 720 may extend from the lip commissure hook or from a portion of the intraoral portion. In some examples, bite stabilizer extends from the flattened edge of lip commissure hook 604, such as left edge 654 (as shown in FIGS. 7B and 7D). In some embodiments, bite stabilizer 720 may provide improved stabilization by interfacing with the user's upper and/or lower teeth 312. For example, user 300 may bite the stabilizer 720 to secure the position of oral interface 700 while in operation. In some embodiments, bite stabilizer 720 may be configured with a customized surface to conform to the particular bite pattern of the user.

In some embodiments bite stabilizer 720 may further comprise on or more edges 722 for further stabilization of the position. Four possible edges are shown in FIG. 7B, including upper edges 722a and 722b, and lower edges 722c and 722d. Any combination of edges may be used in various embodiments. For example, upper and lower edges 722a and 722c on the interior may be configured on bite stabilizer 720 such that the user may further secure oral interface 700 with the tongue. As another example, lower edges 722c and 722d may be configured to form a trough to fit over a row of one or more lower teeth. Similarly, upper edges 722a and 722b may be configured to form a trough to fit around a row of one or more upper teeth. In some embodiments, bite stabilizer 720 and edges 722 may be customized to secure onto particular teeth 312 of the user (shown in dashed lines in FIG. 7B). For example, the trough formed by lower edges 722c and 722d may be customized to snap securely over the row of lower teeth. This may provide a secure fit, reduce unwanted movement of the oral interface, and ensure consistent positioning for every use.

In some embodiments, bite stabilizer 720 is a removable component that may be removed for customization of the oral interface. In other words, a customized bite stabilizer may be manufactured and attached to a standard oral interface. This may reduce manufacturing cost because customizable bite stabilizers can be manufactured separately from a standard oral interface.

In some embodiments, the bite stabilizer may be configured with an electronic input device, such as a controller, switch, or joystick. Such input device may comprise a mechanical or electronic switch or mini-joystick, mounted on the oral interface, in one or more of various different locations. The user could activate such a switch with their tongue, teeth, lips, cheek, chin or other part of their face or mouth that could provide adequate contact to activate the switch or mini-joystick. This would allow the user to control devices, such as an alarm, their wheelchair, environmental controls, etc., with the oral interface, in addition to gas or liquid exchange.

For example, lower edge 722c of bite stabilizer 722 may be configured as an electronic switch with button 724 may be positioned upon edge 722c, as shown in FIG. 7B. Such switch may function as a pressure-sensitive tongue switch which can be activated by the user's tongue by applying pressure with the tongue to depress the switch button 724. For example, the actuation pressure may be approximately 10 ounces. Activation may then stop when the button is released. In some embodiments, the switch may be configured to communicate wirelessly with a user device. A user device may be one of various electronic devices, such as a phone, tablet, mp3 player, or other mobile computing device. In other embodiments, switch 724 is a pivoting stick or mini-joystick. Such an input device with a mini-joystick may comprise a pivoting stick which pivots on a base and reports its angle or direction to the device it is controlling. Thus, when used in conjunction with a SNP controller device, such oral interface would provide increased command and control options and functionality.

In some embodiments, the switch may be configured to form a wired connection with the user device. In such embodiments, the wire may extend from the switch on bite stabilizer 720 in the user's mouth to the corresponding electronic device. In some embodiments, the wire may be attached to various portions of the structure of oral interface 700. FIGS. 7D illustrates edge 722c configured as a switch with button 724 using dashed lines. For example, wire 726 shown in dashed lines in FIG. 7D may extend from lower edge 722c and run along the side of intraoral portion 610, lip commissure hook 604, main body 602, and/or outer mandible contact 620. In some embodiments, wire 726 may be integrated within the structure of oral interface 700. In some embodiments, wire 726 may be positioned through at least a portion of the flow channel.

FIG. 7G illustrates example oral interface 700 worn by a user 300, in accordance with one or more embodiments. In some embodiments, lip guard may be angled to match curvature of face on the. For example, the top view depicted in FIG. 7F shows a top view of oral interface 700 with vertical axis 790, lateral axis 792, and horizontal axis 794 similar to vertical axis 190, lateral axis 192, and horizontal axis 194, respectively. Line 710a represents a flattened plane at the edge of lip guard 710. As shown, lip guard 710 may be angled relative to horizontal axis 794 by angle 710b which is greater than 90 degrees. As such, the lip guard is turned toward the user's lips and mouth to match the contour of the user's face. This further enhances the fit of the oral interface, as well as improves the seal created between the lip guard and the user's lips.

FIG. 7H illustrates another example oral interface 700-A comprising another example lip commissure hook, in accordance with one or more embodiments. Only the main body 702-A, lip commissure hook 704-A, and intraoral portion 710-A are shown in FIG. 7H. As illustrated, lip commissure hook 704-A includes indentations 730 and 732 configured to interface with the users upper and lower lips, respectively. Such indentations may provide improved stabilization during operation, as well as an improved seal for better suction or output of gases or fluids. In some embodiments, indentations 730 and 732 may be implemented with an unflattened lip commissure hook. In some embodiments, indentations 730 and 732 may be implemented with a lip guard. In some embodiments, only one of the indentations may be implemented instead of both.

With reference to FIGS. 8A-8C, shown are various perspective views of another example oral interface with a modified intraoral portion. FIG. 8A illustrates a left side view of oral interface 800, FIG. 8B illustrates a right side view of oral interface 800, and FIG. 8C illustrates a right side view of another oral interface 800-A. Only the main body 802, lip commissure hook 804, and intraoral portion 810 are shown in FIGS. 8A-8C. It should be understood that oral interfaces shown in FIGS. 8A-8C may instead comprise any one of the outer mandible contact embodiments described herein or no outer mandible contact at all.

In various embodiments, oral interface 800 comprises a broadened intraoral portion 810. In some embodiments, broadened intraoral portion 810 may provide more secure positioning within the user's mouth by creating a larger surface area that is easier to position between the teeth and the cheek. In some embodiments, intraoral portion 810 may comprise smooth surfaces on each side. A smooth surface on the left side shown in FIG. 8A would prevent the teeth from catching on the surface during movement of the jaw. A smooth surface on the right side shown in FIG. 8B would also provide a comfortable interface surface against the user's inner cheek. In some embodiments, oral interface 800 may also comprise an inner mandible contact portion 812 on intraoral portion 810 where the oral interface rests against the user's gums or teeth.

In some embodiments, intraoral portion 810 may be narrowed to fit comfortably between the inner cheek and jaw of the user. As such, the portion of flow channel 840 corresponding to intraoral portion 810 will also be narrowed. Flow channel 840 is shown in dashed lines in FIG. 8B. Such portion of flow channel 840 may also be widened to maintain the total cross-sectional area of the flow channel to maintain a suitable flow rate of air or fluids. This would allow the entire intraoral portion 810 to have a flattened geometry, instead of a tubular straw structure, which may enhance comfort during operation. However, in some embodiments, the oral interface may maintain a more tubular geometry. As shown in FIG. 8C, broadened intraoral portion 810-A of oral interface 800-A still includes a tubular portion allowing flow channel 840-A which is similar to the other flow channels described herein.

In some embodiments, intraoral portion 810 is configured with additional openings 846 to soften or disperse the exiting pressure of air or fluid. The additional openings 846 also provide alternate passageways in case one or more other openings become blocked during operation.

Figure 9:
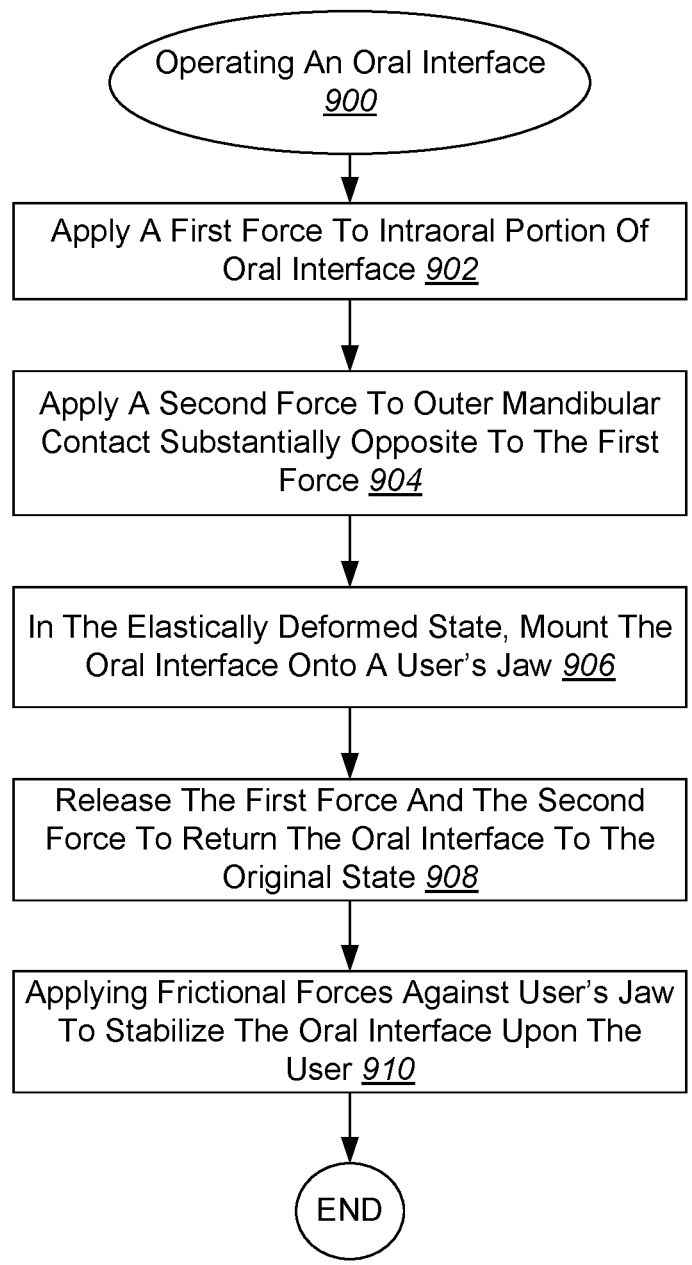
FIG. 9 illustrates an example method for operating an oral interface, in accordance with one or more embodiments.

FIG. 9 is an example method 900 for operating an oral interface, in accordance with one or more embodiments. FIG. 9 will be described with reference to oral interface 600. However, it should be recognized that method 900 may be implemented with any one of the oral interfaces described herein. At step 902, a first force is applied to an intraoral portion of the oral interface, such as intraoral portion 610.

At step 904, a second force is applied to an outer mandibular contact, such as outer mandibular contact 620. In some embodiments, the second force is substantially opposite to the first force. In some embodiments, the first force and the second force cause the oral interface to elastically deform from an original state to an elastically deformed state. For example, in the elastically deformed state, the spacing between various portions of the oral interface, such as gaps 150 and 152, may increase in size to allow easier application onto the user's face.

At step 906, the oral interface is mounted onto a user's jaw when the oral interface is in the elastically deformed state. In some embodiments, the outer mandibular contact rests against a first portion of the user's jaw located outside of the user's mouth, as shown in FIGS. 5A and 5B with outer mandibular contact 420 and outer mandible 320. In some embodiments, the intraoral portion rests against a second portion of the user's jaw located in the user's mouth, as shown in FIGS. 5A and 5B with intraoral portion 410 and inner mandible 310. In some embodiments, the inner mandible contact of the intraoral portion rests against the inner mandible. At step 908, the first force and the second force are released to return the oral interface to the original state. Once the oral interface returns to the original state, the intraoral portion and the outer mandibular contact apply frictional forces against the user's jaw and cheek to stabilize the oral interface upon the user at step 910.

In particular embodiments, the oral interface does not need to be deformed in order to mount the oral interface onto the user's jaw. For example, the intraoral portion may simply be positioned against the appropriate portion of inner mandible 310, and the outer mandible contact may be positioned against the appropriate portion of outer mandible 320. Then, via movement of the user's jaw and lips, the oral interface may be correctly positioned and secured onto the user's jaw. In yet other embodiments, where the oral interface comprises material with malleable characteristics. The first or second forces may be applied to reshape the oral interface from the original state to the deformed state, such as to increase the size of gaps 150 or 152 for easier attachment onto the user's face. Once in position, additional forces may be applied to the oral interface to reshape the various portions to a subsequent deformed state, which may or may not be the same as the original state.

Figure 10A:
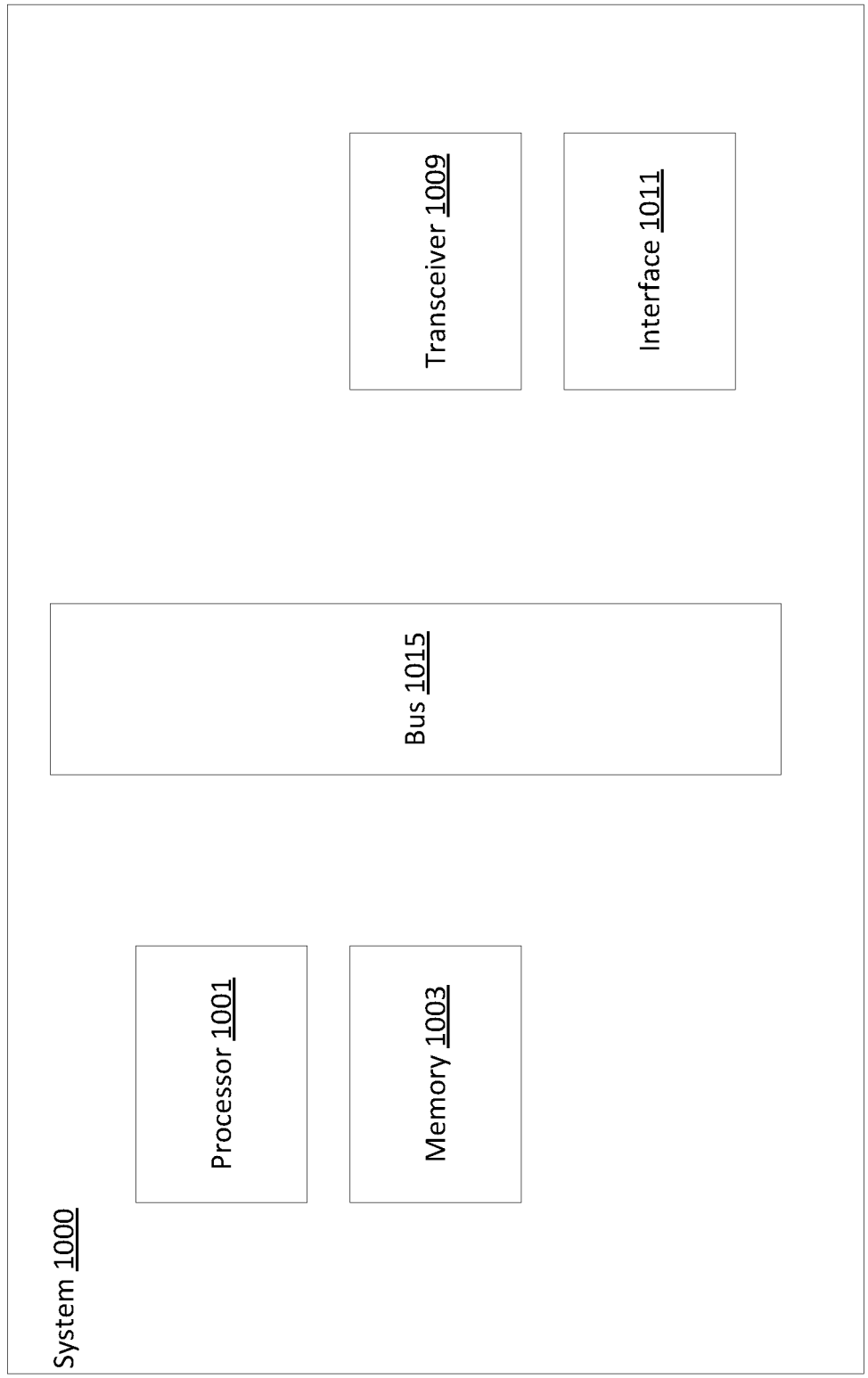
FIG. 10A is a block diagram illustrating an example of a system which may implement various apparatus described in the present disclosure.

Various computing devices can implement the methods and systems described herein. For instance, a mobile device, computer system, etc. can be used to implement a wireless or wired switch of an oral interface. With reference to FIG. 10A, shown is a particular example of a computer system 1000 that can be used to implement particular examples of the present disclosure. According to particular example embodiments, a system 1000 suitable for implementing particular embodiments of the present disclosure includes a processor 1001, a memory 1003, a transceiver 1009, an interface 1011, and a bus 1015 (e.g., a PCI bus). When acting under the control of appropriate software or firmware, the processor 1001 is responsible for processing inputs such as converting activation of switches to electrical and wireless signals. Various specially configured devices can also be used in place of a processor 1001 or in addition to processor 1001. The complete implementation can also be done in custom hardware.

The interface 1011 is typically configured to send and receive data packets or data segments over a network, such as Wi-Fi or Bluetooth. Particular examples of interfaces the device supports include Ethernet interfaces, frame relay interfaces, cable interfaces, DSL interfaces, token ring interfaces, and the like. Alternatively, interface 1011, may be configured to interface with other computing devices via wired-based communication technology. The interface 1011 may include separate input and output interfaces, or may be a unified interface supporting both operations. In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media.

In some cases, they may also include an independent processor and, in some instances, volatile RAM. The independent processors may control such communications intensive tasks as packet switching, media control and management.

Transceiver 1009 is typically a combination transmitter/receiver device. However system 1000 may include a transmitter and a receiver as separate components in some embodiments. Transceiver 1009 may be configured to transmit and/or receive various wireless signals, including Wi-Fi, Bluetooth, etc. In some embodiments, system 1000 may function as a wireless switch to transmit commands to electronic devices via wireless signals. In various embodiments, transceiver 1009 may operate in a half duplex or full duplex mode. Various protocols could be used including various flavors of Bluetooth, Wi-Fi, light of sight transmission mechanisms, passive and active RFID signals, cellular data, mobile-satellite communications, as well as LPWAN, GPS, and other networking protocols. According to various embodiments, the transceiver may operate as a Bluetooth or Wi-Fi booster or repeater.

According to particular example embodiments, the system 1000 uses memory 1003 to store data and program instructions for operations including transmission of control signals. The program instructions may control the operation of an operating system and/or one or more applications, for example. The memory or memories may also be configured to store received metadata and batch requested metadata. The memory or memories may also be configured to store data corresponding to parameters and weighted factors.

Because such information and program instructions may be employed to implement the systems/methods described herein, the present disclosure relates to tangible, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

Figure 10B:
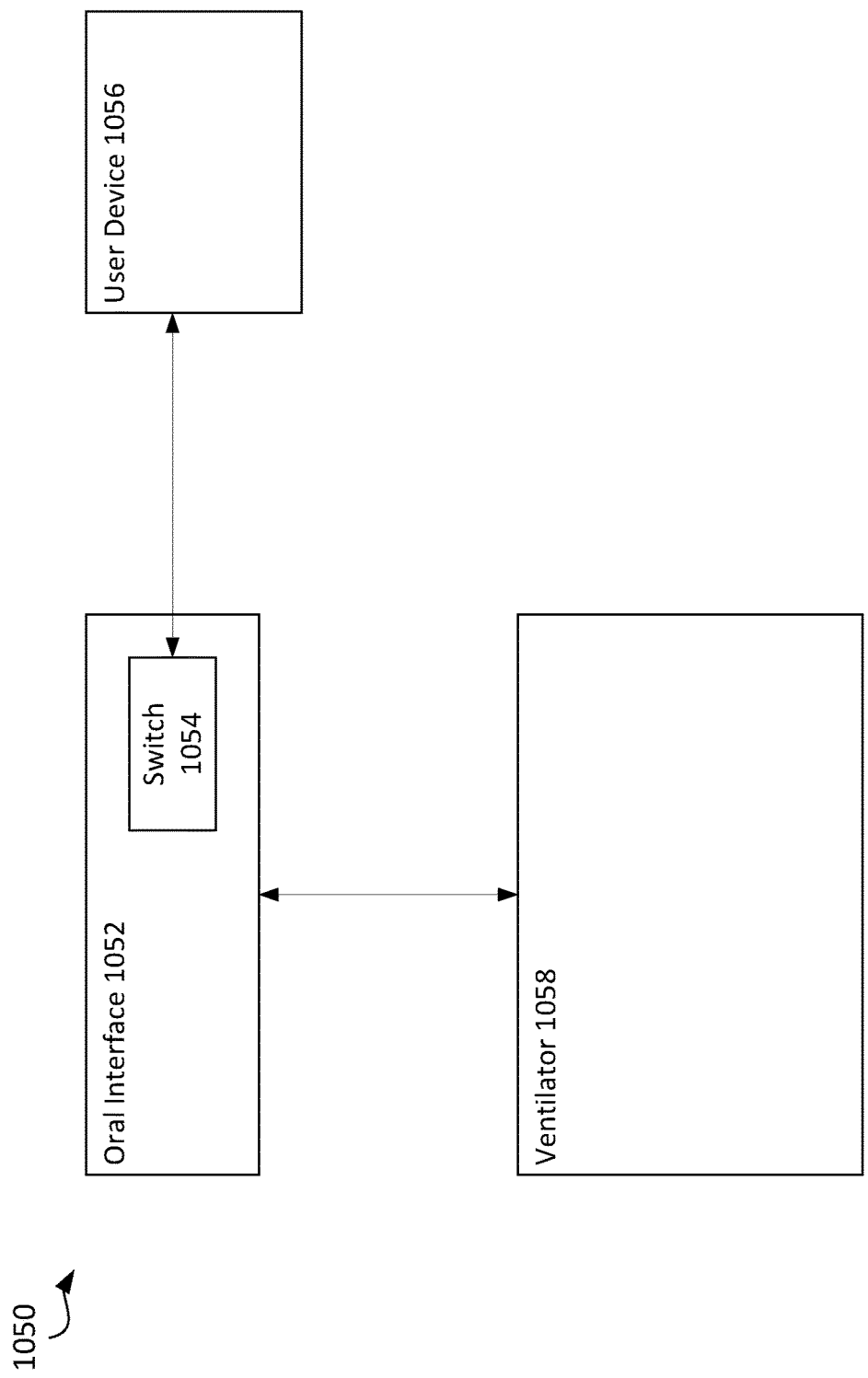
FIG. 10B is a block diagram illustrating an example ventilator system which may be implemented using various embodiments of the present disclosure.

FIG. 10B is a block diagram illustrating an example ventilator system 1050 which may be implemented using various embodiments of the present disclosure. In various embodiments, system 1050 comprises oral interface 1052 coupled to ventilator 1058. Oral interface 1052 may be coupled to ventilator via a tube or hose such that air from the ventilator is directed toward the oral interface where it may enter a user's mouth. In some embodiments, oral interface 1052 may further comprise switch 1054, which may be a tongue switch as described herein. Such switch may communicate with user device 1056 wirelessly, or through a wired connection to perform various operations on the user device, which may be a mobile phone, tablet, or other computing device or electronic device.

Although many of the components and processes are described above in the singular for convenience, it will be appreciated by one of skill in the art that multiple components and repeated processes can also be used to practice the techniques of the present disclosure.

While the present disclosure has been particularly shown and described with reference to specific embodiments thereof, it will be understood by those skilled in the art that changes in the form and details of the disclosed embodiments may be made without departing from the spirit or scope of the disclosure. It is therefore intended that the disclosure be interpreted to include all variations and equivalents that fall within the true spirit and scope of the present disclosure.

What is claimed is:

1. An oral interface comprising:
    a body comprising a flow channel extending through the body from a first opening to a second opening;
    a lip commissure hook extending from a first end of the body in a curved configuration;
    an intraoral portion extending from the lip commissure hook to form a gap between the intraoral portion and the body, wherein the flow channel extends through the lip commissure hook and the intraoral portion to the first opening;
    an outer mandibular contact extending from the body, wherein the outer mandibular contact is configured to rest against a first portion of a user's mandible located outside of the user's mouth;
    a bite stabilizer extending from the intraoral portion and configured to interface with the user's teeth when the oral interface is worn, wherein the bite stabilizer comprises:
        a horizontal platform structure, and a first edge and a second edge extending from the horizontal platform structure forming a trough configured to secure onto a row of one or more lower teeth of the user,
        wherein when the oral interface is worn, a bottom surface of the horizontal platform structure is configured to interface with an occlusal surface of the row of one or more lower teeth, an upper surface of the horizontal platform structure is configured to interface with an occlusal surface of a row of one or more upper teeth of the user, the first edge is positioned against a facial surface of the row of one or more lower teeth, and the second edge is positioned against a lingual surface of the row of one or more lower teeth; and
    a switch positioned on the second edge such that the switch is located between the lingual surface of the row of one or more lower teeth and the user's tongue when the oral interface is worn, wherein the switch is communicatively coupled to a user device.

2. The oral interface of claim 1, wherein the intraoral portion and the outer mandibular contact are configured to apply frictional forces against the user's cheek and mandible, respectively, to stabilize the oral interface upon the user.

3. The oral interface of claim 1, wherein the outer mandibular contact is configured to apply a force against a first portion of the user's mandible located outside of the user's mouth.

4. The oral interface of claim 3, wherein the outer mandibular contact comprises a surface that is customized to conform to a particular shape of the first portion of the user's mandible.

5. The oral interface of claim 3, wherein the outer mandibular contact comprises material of a form of rubber.

6. The oral interface of claim 3, wherein the intraoral portion further comprises an inner mandibular contact including a second surface configured to rest against a second portion of the user's mandible located within the user's mouth.

7. The oral interface of claim 6, wherein the inner mandibular contact comprises a surface that is customized to conform to a particular geometry of teeth or gums of the second portion of the user's mandible.

8. The oral interface of claim 6 wherein the oral interface comprises an elastically deformable flexible material.

9. The oral interface of claim 8,
wherein the oral interface is configured to elastically deform from an original state to an elastically deformed state in response to an applied force in order to mount the oral interface onto the first portion and the second portion of the user's mandible, and
wherein upon removal of the applied force, the oral interface is configured return to the original state to apply frictional forces against the user's mandible and cheek.

10. The oral interface of claim 1, wherein the outer mandibular contact is integrated with the body such that the flow channel extends through the outer mandibular contact.

11. The oral interface of claim 1, wherein the body further comprises a connector portion extending from a second end of the body, the connector portion including the second opening interconnected with the flow channel.

12. The oral interface of claim 11, wherein the second opening is configured to be coupled to a ventilator hose or hose connector.

13. The oral interface of claim 1, wherein the lip commissure hook comprises a flattened surface configured to interface with the user's lips.

14. The oral interface of claim 1, wherein the intraoral portion comprises one or more additional openings interconnected with the flow channel.

15. The oral interface of claim 1, wherein the oral interface allows bidirectional flow of air through the flow channel from the first opening to the second opening.

16. The oral interface of claim 1,
wherein the intraoral portion extends from the lip commissure hook at an angle relative to a midline axis of the oral interface such that the intraoral portion is angled away from a center of the user's mouth when the oral interface is worn.

17. The oral interface of claim 16, further comprising:
a lip guard comprising a flattened panel structure extending from the lip commissure hook and surrounding the lip commissure hook;
wherein the lip guard comprises a labial surface that faces the user's lips when the oral interface is worn, wherein the labial surface is configured to interface with the user's lips and lip commissure to form a seal; and
wherein the lip guard is angled with respect to the midline axis such that the labial surface is angled toward the center of the user's mouth when the oral interface is worn.

18. A system comprising:
a ventilator; and
an oral interface coupled to the ventilator via a hose, the oral interface comprising:
a body comprising a flow channel extending through the body from a first opening to a second opening;
a lip commissure hook extending from a first end of the body in a curved configuration;
an intraoral portion extending from the lip commissure hook to form a gap between the intraoral portion and the body, wherein the flow channel extends through the lip commissure hook and the intraoral portion to the first opening;
an outer mandibular contact extending from the body, wherein the outer mandibular contact is configured to rest against a first portion of a user's mandible located outside of the user's mouth
a bite stabilizer extending from the intraoral portion and configured to interface with a user's teeth when the oral interface is worn, wherein the bite stabilizer comprises:
a horizontal platform structure, and a first edge and a second edge extending from the horizontal platform structure forming a trough configured to secure onto a row of one or more lower teeth of the user,
wherein when the oral interface is worn, a bottom surface of the horizontal platform structure is configured to interface with an occlusal surface of the row of one or more lower teeth, an upper surface of the horizontal platform structure is configured to interface with an occlusal surface of a row of one or more upper teeth of the user, the first edge is positioned against a facial surface of the row of one or more lower teeth, and the second edge is positioned against a lingual surface of the row of one or more lower teeth; and
a switch positioned on the second edge such that the switch is located between the lingual surface of the row of one or more lower teeth and the user's tongue when the oral interface is worn, wherein the switch is communicatively coupled to a user device.

19. A method of operating an oral interface, the method comprising:
positioning an intraoral portion of the oral interface against a first portion of a user's jaw located within the user's mouth, wherein the oral interface comprises a body and a lip commissure hook extending from a first end of the body in a curved configuration, wherein the intraoral portion extends from the lip commissure hook to form a gap between the intraoral portion and the body, wherein a flow channel extends through the body, the lip commissure hook, and the intraoral portion to a first opening; and
positioning an outer mandibular contact of the oral interface against a second portion of the user's jaw located outside the user's mouth, wherein the outer mandibular contact extends from the body; and
securing a bite stabilizer onto a row of one or more lower teeth of the user, wherein the bite stabilizer extends from the intraoral portion, wherein the bite stabilizer comprises:
a horizontal platform structure,
a first edge and a second edge extending from the horizontal platform structure forming a trough configured to secure onto the row of one or more lower teeth of the user, wherein when the oral interface is worn, a bottom surface of the horizontal platform structure is configured to interface with an occlusal surface of the row of one or more lower teeth, an upper surface of the horizontal platform structure is configured to interface with an occlusal surface of a row of one or more upper teeth of the user, the first edge is positioned against a facial surface of the row of one or more lower teeth, and the second edge is positioned against a lingual surface of the row of one or more lower teeth, and
a switch positioned on the second edge such that the switch is located between the lingual surface of the row of one or more lower teeth and the user's tongue when the oral interface is worn, wherein the switch is communicatively coupled to a user device.

20. The method of claim 19, further comprising:
applying a first force to an intraoral portion of the oral interface;
applying a second force to an outer mandibular contact, wherein the second force includes a directional element that is opposite to the first force, wherein the first force and the second force cause the oral interface to elastically deform from an original state to an elastically deformed state;
when the oral interface is in the elastically deformed state, positioning the intraoral portion against the first portion of the user's jaw, and positioning the outer mandibular contact against the second portion of the user's jaw; and
releasing the first force and the second force to return the oral interface to the original state such that the intraoral portion and the outer mandibular contact apply frictional forces against the user's cheek and jaw, respectively, to stabilize the oral interface upon the user.

\* \* \* \* \*